(12) United States Patent  (10) Patent No.: US 7,816,335 B2
Wight et al.  (45) Date of Patent: Oct. 19, 2010

(54) THERAPEUTIC COMPOUNDS AND METHODS

(76) Inventors: Thomas N. Wight, 6524 44th Ave. NE., Seattle, WA (US) 98115; Mervyn Merrilees, 207 Eskdale Road, Birkenhead, Auckland (NZ)

( * ) Notice: Subject to any disclaimer, the term of this patent is extended or adjusted under 35 U.S.C. 154(b) by 0 days.

(21) Appl. No.: 10/270,253

(22) Filed: Oct. 11, 2002

(65) Prior Publication Data
US 2004/0213762 A1 Oct. 28, 2004

Related U.S. Application Data

(63) Continuation of application No. PCT/US01/11940, filed on Apr. 12, 2001.

(60) Provisional application No. 60/196,805, filed on Apr. 13, 2000.

(51) Int. Cl.
A61K 31/70 (2006.01)
A01N 43/04 (2006.01)
C07H 21/02 (2006.01)
C07H 21/04 (2006.01)

(52) U.S. Cl. ........................ 514/44; 536/23.1
(58) Field of Classification Search ............ 514/44; 536/24.1, 23.1
See application file for complete search history.

(56) References Cited

U.S. PATENT DOCUMENTS 5,180,808 A 1/1993 Ruoslahti ............... 530/350
5,635,370 A 6/1997 Hockfield et al. .......... 435/69.1

FOREIGN PATENT DOCUMENTS

WO WO-91/08230 A1 6/1991
WO WO-00/68361 A1 11/2000
WO WO-0179284 A2 10/2001

OTHER PUBLICATIONS

Anderson, WF. Human Gene Therapy. Nature, 1998 vol. 392 (6679 Suppl):25-30.*
Anderson, WF. The Current Status of Clinical Gene Therapy. Human Gene Therapy, 2002 vol. 13:1261-1262.*
Crystal, R. Transfer of Genes to Humans: Early Lessons and Obstacles to Success. Science, 1995 vol. 270:404-410.*
Branch, A. A Good Antisense Molecule is Hard to Find. TIBS, Feb. 1998 vol. 23, pp. 45-50.*
Bowie et al., 1990. Science, vol. 247, pp. 1306-1310. Deciphering the Message in Protein Sequences: Tolerance to Amino Acid Substitutions.*
Nyberg et al. (Molecular Therapy, 2004 vol. 10: No. 6, pp. 976-980) Workshop on Long-term Follow-up of Participants in Human Gene Transfer Research.*
The Times Article (Apr. 14, 2009), Mark Henderson, Science Editor. Analysis: Gene therapy has immense potential After almost two decades, gene therapies have recently started to deliver on their promise.*

(Continued)

Primary Examiner—Sean McGarry
Assistant Examiner—Terra Cotta Gibbs
(74) Attorney, Agent, or Firm—Schwegman, Lundberg & Woessner, P.A.

(57) ABSTRACT

Therapeutic agents and methods useful to modulate the activity of V3.

32 Claims, 17 Drawing Sheets

OTHER PUBLICATIONS

Cleary, E. G., et al., "Chapter 4. Elastic Tissue, Elastin and Elastin Associated Microfibrils", *In Extracellular Matrix, vol. 2, Molecular Components and Interactions*, Edited by Wayne D. Comper, Published by Overseas Publishers Association,(1996),95-140.

Dours-Zimmermann, M. T., et al., "A Novel Glycosaminoglycan Attachment Domain Identified in Tow Alternative Splice Variants of Human Versican", *Journal of Biological Chemistry*, 269(52), (Dec. 30, 1994),32992-32998.

Lemire, J. M., et al., "Versican/PG-M Isoforms in Vascular Smooth Muscle Cells", *Arteriosclerosis, Thrombosis & Vascular Biology*, 19(7), (1999),1630-1639.

Leonardi, R., et al., "Immunolocalization of CD44 Adhesion Molecules in Human Periradicular Lesions", *Oral Surgery, Oral Medicine, Oral Pathology and Endodontics*, 89(4), (2000),480-485.

Merrilees, M., et al., "Alteration of Smooth Muscle Cell Phenotype Through Retroviral Insertion of the Gene for Versican Variant V3", *Proceedings of the MBSANZ*, 3, Pan Pacific Connective Tissue Societies Symposium, Queenstown, NZ, Nov. 1999 (Abstract Only), 1 Page.

Naso, M. F., et al., "Characterization of the complete genomic structure of the human versican gene and functional analysis of its promoter", *Journal of Biological Chemistry*, 269(52), (1994),32999-33008.

Paulus, W., et al., "Differential Expression of Versican Isoforms in Brain Tumors", *Journal of Neuropathology & Experimental Neurology*, 55(5), (1996),528-33.

Schmalfeldt, M., et al., "Brain Derived Versican V2 is a Potent Inhibitor of Axonal Growth", *Journal of Cell Science*, 113 (Part 5), (2000),807-816.

Wight, T. N., "Proteoglycans Are Extracellular Matrix (ECM) Molecules That Influence Multiple Events in Atherosclerosis and Restenosis", (Abstract Only),1 Page.

Wight, T. N., "Proteoglycans in Atherosclerosis and Restenosis", (Abstract Only),1 Page.

Wight, T., et al., "The Role of Matrix in In-Stent Restenosis and Restenosis After Balloon Angioplasty", (Abstract Only) Presented at the 6th International Drug Delivery Meeting, Geneva, Switzerland, Jan. 27, 2000,1 page.

Zako, M., et al., "Expression of PG-M(V3), an Alternatively Spliced Form of PG-M without a Chondroitin Sulfate Attachment Region in Mouse and Human Tissues", *Journal of Biological Chemistry*, 270(8), (Feb. 24, 1995),3914-3918.

Zimmermann, D. R., et al., "Versican is Expressed in the Proliferating Zone in the Epidermis and in Association with the Elastic Network of Dermis", *J. of Cell Biology*, vol. 124, No. 5, (Mar. 1994),817-825.

Zako, M., et al., "Human pgH3 mRNA for proteoglycan PG-M(V3), complete cds.", *EMBL/Gen Bank/DDBJ Database*, D32039—Accession Number, http://www.ncbi.nlm.nih.gov/entrez/viewer.fcgi?db=nucleotide&val=1008912,(Oct. 5, 1995).

Wight, T. N., "Proteoglycans Are Extracellular Matrix (ECM) Molecules That Influence Multiple Events in Atherosclerosis and Restenosis", *Proceedings, 11th International Vascular Biology Meeting*, 32(3), (Sep. 5-9, 2000, Geneva, Switzerland) (Abstract Only),(2000), p. S085.

Wight, T. N., "Proteoglycans in Atherosclerosis and Restenosis", *Atherosclerosis*, 151(1), (Abstract Only),(2000), p. 87.

"Australian Application Serial No. 2001253408, Examiner's First Report on Voluntary Request to Amend Patent mailed May 15, 2008", 6 pgs.

"Australian Application Serial No. 2001253408, Examiner's Second Report on Voluntary Request to Amend Patent mailed Jun. 12, 2008", 7 pgs.

"Australian Application Serial No. 2001253408, Response filed Mar. 7, 2007 to Examiner's First Report mailed Jun. 23, 2005", 16 pgs.

"Australian Application Serial No. 2001253408, Response filed Mar. 22, 2007 to Examiner's Second Report mailed Mar. 16, 2007", 12 pgs.

"Australian Application Serial No. 2001253408, Examiner's First Report mailed Jun. 23, 2005", 9 pgs.

"Australian Application Serial No. 2001253408, Examiner's Second Report mailed Mar. 16, 2007", 13 pgs.

"Australian Application Serial No. 2001253408, Response filed Jun. 6, 2008 to Examiner's First Report on Voluntary Request to Amend Patent mailed May 15, 2008", 11 pgs.

"Canadian Application Serial No. 2,406,192, Response filed May 12, 2009 to Office Action mailed Nov. 12, 2008", 20 pgs.

"Canadian Application Serial No. 2,406,192,Office Action mailed Nov. 12, 2008", 3 pgs.

"European Application Serial No. 01926904.2, Examination Report mailed May 12, 2006", 5 pgs.

"European Application Serial No. 01926904.2, First Examination Report mailed Nov. 15, 2005", 6 pgs.

"European Application Serial No. 01926904.2, Invitation mailed Oct. 22, 2008", 2 pgs.

"European Application Serial No. 01926904.2, Response filed Jan. 9, 2008 to Invitation mailed Jun. 9, 2007", 8 pgs.

"European Application Serial No. 01926904.2, Response filed Mar. 25, 1006 to First Examination Report mailed Nov. 15, 2005", 5 pgs.

"European Application Serial No. 01926904.2, Response filed Nov. 5, 2008 to Invitation mailed Oct. 22, 2008", 27 pgs.

"European Application Serial No. 01926904.2, Response filed Nov. 8, 2006 to Examination Report mailed May 12, 2006", 7 pgs.

"European Application Serial No. 01926904.2, Office Action mailed Mar. 11, 2009", 3 pgs.

"International Application Serial No. PCT/US01/11940, International Preliminary Examination Report mailed Aug. 7, 2002", 3 pgs.

"International Application Serial No. PCT/US01/11940, Written Opinion mailed Jun. 14, 2002", 2 pgs.

Consiglio, A., et al., "In vivo gene therapy of metachromatic leukodystrophy by lentiviral vectors: correction of neuropathology and protection against learning impairments in affected mice", *Nat. Med.*, 7(3), (Abstract Only), (2001), 1 pg.

Densmore, C. L., et al., "Gene transfer by guanidinium-cholesterol: dioleoylphosphatidyl-ethanolamine liposome-DNA complexes in aerosol", *J. Gene Med.*, 1(4), (Abstract Only), (1999), 1 pg.

Goerner, M., et al., "Expansion and transduction of noneriched human cord blood cells using HS-5 conditioned medium and FLT3-L", *Hematother. Stem Cell Res.*, 9(5), (Abstract Only), (2000), 1 pg.

Gregoriadis, G., "DNA vaccines: a role for liposomes", *Curr. Opin. Mol. Ther.*, 1(1), (1999), 1 pg.

Hoelters, J., et al., "Nonviral genetic modification mediates effective transgene expression and functional RNA interference in human mesenchymal stem cells", *J. Gene. Med.*, 7(6), (Abstract Only), (2005), 1 pg.

Horowitz, J., et al., "Adenovirus-mediated p53 gene therapy: overview of preclinical studies and potential clinical applications", *Curr. Opin. Mol. Ther.*, 1(4), (Abstract Only), (1999), 1 pg.

Ilan, Y., "Technology evaluation: naked DNA", *Curr. Opin. Mol. Ther.*, 1(1), (Abstract Only), (1999), 1 pg.

Jayakumar, J., et al., "Gene therapy for myocardial protection: transfection of donor hearts with heat shock protein 70 gene protects cardiac function against ischemia-reperfusion injury", *Circulation*, (19, Suppl.3), (Abstract Only), (2000), 1 pg.

Johnson, L. G., et al., "Pseudotyped human lentiviral vector-mediated gene transfer to airway epithelia in vivo", *Gene Therapy*, 7(7), (2000), 568-574.

Kreiss, P., et al., "Erythropoietin secretion and physiological effect in mouse after intramuscular plasmid DNA electrotransfer", *J. Gene Med.*, 1(4), (Abstract Only), (1999), 1 pg.

Lee, L. Y., et al., "Exogenous Control of Cardiac Gene Therapy: Evidence of Regulated Myocardial Transgene Expression After Adenovirus and Adeno-Associated Virus Transfer of Expression Cassettes Containing Corticosteroid Response Element Promoters", *The Journal of Thoracic and Cardiovascular Surgery*, 118, (1999), 26-35.

McCluskie, M. J., et al., "Novel strategies using DNA for the induction of muscosal immunity", *Crit. Rev. Immunol.*, 19(4), (Abstract Only), (1999), 1 pg.

McCluskie, M. J., et al., "Route and Method of Delivery of DNA Vaccine Influence Immune Responses in Mice and Non-Human Primates", *Molecular Medicine*, 5(5), (1999), 287-300.

Nuss, H. B., et al., "Reversal of Potassium Channel Deficiency in Cells from Failing Hearts by Adenoviral Gene Transfer: A Prototype for Gene Therapy for Disorders of Cardiac Excitability and Contractility", *Gene Therapy*, 3(10), (1996), 900-912.

Rovira, A., et al., "Stable in vivo expression of glucose-6-phosphate dehydrogenase (G6PD) and rescue of G6PD deficiency in stem cells by gene transfer", *Blood*, 96(13), (Abstract Only), (2000), 1 pg.

Sawamura, D., et al., "In vivo gene introduction into keratinocytes using jet injection", *Gene Ther.*, 6(10), (Abstract Only), (1999), 1 pg.

Sosnowski, B. A., et al., "FGF2-targeted adenoviral vectors for systemic and local disease", *Curr. Opin. Mol. Ther.*, 1(5), (Abstract Only), (1999), 1 pg.

Yoshida, M., et al., "In vivo gene transfer of an extracellular domain of platelet-derived growth factor beta receptor by the HVJ-liposome method ameliorates bleomycin-induced pulmonary fibrosis", *Biochem. Biophy. Res. Commun.*, 265(2), (Abstract Only), (1999), 1 pg.

* cited by examiner

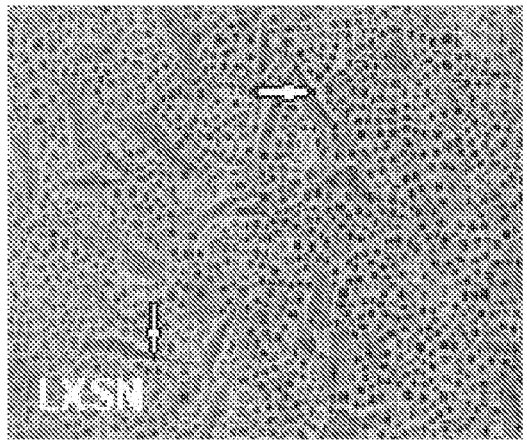 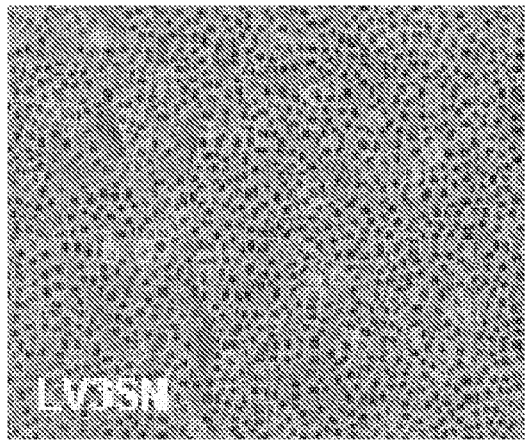
FIG. 9A  FIG. 9B
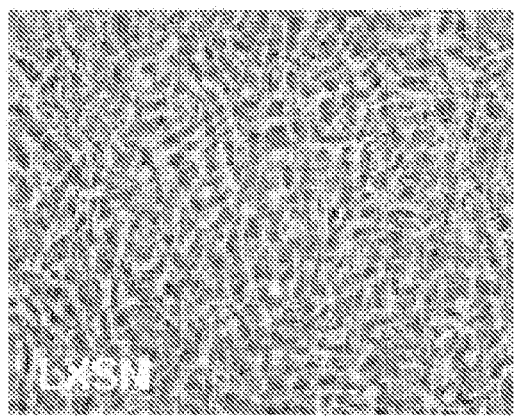 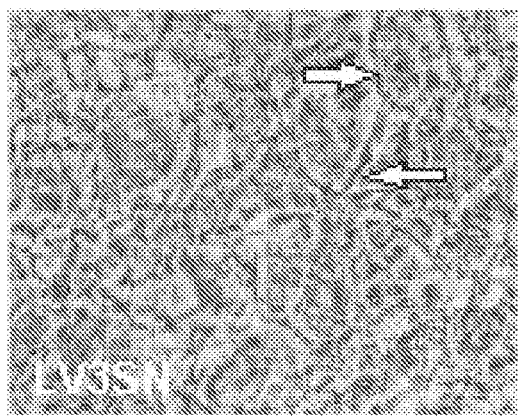
FIG. 10A  FIG. 10B

Sequence of human V3 from D32039

```
   1 caccaagctt cctatgtgac ccgctgggc aacgccgaac ccagtcgcgc agcgctgcag
  61 tgaattttcc cccaaactg caataagccg ccttccaagg ccaagatgtt cataaatata
 121 aagagcatct tatggatgtg ttcaacctta atagtaaccc atgcgctaca taaagtcaaa
 181 gtgggaaaaa gcccaccggt gaggggctcc ctctctggaa aagtcagcct accttgtcat
 241 ttttcaacga tgcctacttt gccacccagt tacaacacca gtgaatttct ccgcatcaaa
 301 tggtctaaga ttgaagtgga caaaatgga aaagatttga aagagactac tgtccttgtg
 361 gcccaaaatg gaaatatcaa gattggtcag gactacaaag ggagagtgtc tgtgcccaca
 421 catcccgagg ctgtgggcga tgcctccctc actgtggtca agctgctgga aagtgatgcg
 481 ggtctttacc gctgtgacgt catgtacggg attgaagaca cacaagacac ggtgtcactg
 541 actgtggatg gggttgtgtt tcactacagg gcggcaacca gcaggtacac actgaatttt
 601 gaggctgctc agaaggcttg tttggacgtt ggggcagtca tagcaactcc agagcagctc
 661 tttgctgcct atgaagatgg atttgagcag tgtgacgcag gctggctggc tgatcagact
 721 gtcagatatc ccatccgggc tccagagta ggctgttatg gagataagat gggaaaggca
 781 ggagtcagga cttatggatt ccgttctccc caggaaactt acgatgtgta ttgttatgtg
 841 gatcatctgg atggtgatgt gttccacctc actgtcccca gtaaattcac cttcgaggag
 901 gctgcaaaag agtgtgaaaa ccaggctgcc aggctggcaa cagtgggga actccaggcg
 961 gcatggagga acggctttga ccagtgagat tacgggtggc tgtcggatgc cagcgtgcgc
1021 caccctgtga ctgtggccag ggccacgtgt ggaggtggtc tacttgggct gagaaccctg
1081 tatcgttttg agaaccagac aggcttccct cccctggata gcagatttga tgcctactgc
1141 tttaaacgac ctgatcgctg caaaatgaac ccgtgcctta acggaggcac ctgttatcct
1201 actgaaactt cctacgtatg cacctgtgtg ccaggataca ggggagacca gtgtgaactt
1261 gattttgatg aatgtcactc taatccctgt cgtaatggag ccacttgtgt tgatggttt
1321 aacacattca ggtgcctctg ccttccaagt tatgttggtg cacttgtga gcaagatacc
1381 gagacatgtg actatggctg gcacaaattc caagggcagt gctacaaata tttgccccat
1441 cgacgcacat gggatgcagc tgaacgggaa tgccgtctgc agggtgccca tctcacaagc
1501 atcctgtctc acgaagaaca aatgttttgt aatcgtgtgg gccatgatta tcagtggata
1561 ggcctcaatg acaagatgtt tgagcatgac ttcgttgga ctgatggcag cacactgcaa
1621 tacgagaatt ggagacccaa ccagccagac agcttcttt ctgctggaga agactgtgtt
1681 gtaatcattt ggcatgagaa tggccagtgg aatgatgttc ctgcaatta ccatctcacc
1741 tatacgtgca agaaaggaac agttgcttgc ggccagcccc ctgttgtaga aaatgccaag
1801 acctttggaa agatgaaacc tcgttatgaa atcaactccc tgattagata ccactgcaaa
1861 gatggtttca tccaacgtca ccttccaact atccggtgct taggaaatgg aagatgggct
1921 ataccaaaa ttacctgcat gaacccatct gcataccaaa ggacttattc tatgaaatac
1981 tttaaaaatt cctcatcagc aaaggacaat tcaataaata catccaaaca tgatcatcgt
2041 tggagccgga ggtggcagga gtcgaggcgc tgatccctaa aatggcg
``` cDNA polynucleotide sequence for human versican V3 (PG-M(V3)). Accession number D32039 (SEQ ID NO:1)

FIG. 18

Sequence of human V3 from D32039

```
  1 MFINIKSILW MCSTLIVTHA LHKVKVGKSP PVRGSLSGKV SLPCHFSTMP TLPPSYNTSE
 61 FLRIKWSKIE VDKNGKDLKE TTVLVAQNGN IKIGQDYKGR VSVPTHPEAV GDASLTVVEL
121 LASDAGLYRC DVMYGIEDTQ DTVSLTVDGV VFHYRAATSR YTLNFEAAQK ACLDVGAVIA
181 TPRQLPAAYE DGFEQCDAGW LADQTVRYPI RAPRVGCYGD KMGKAGVRTY GFRSPQETYD
241 VYCYVDHLDG DVFHLTVPSK FTFEEAAKEC ENQAARLATV GELQAAWRNG FDQCDYGWLS
301 DASVRHPVTV ARAQCGGGLL GVRTLYRFEN QTGFPPPDSR FDAYCFKRPD RCKMNPCLNG
361 GTCYPTETSY VCTCVPGYSG DQCELDFDEC HSNPCRNGAT CVDGFNTFRC LCLPSYVGAL
421 CEQDTETCDY GWHKFQGQCY KYFAHRRTWD AAERECRLQG AHLTSILSHE EQMFVNRVGH
481 DYQWIGLNDK MFEHDFRWTD GSTLQYENWR PNQPDSFFSA GEDCVVIIWH ENGQWNDVPC
541 NYHLTYTCKK GTVACGQPPV VENAKTFGKM KPRYEINSLI RYHCKDGFIQ RHLPTIRCLG
601 NGRWAIPKIT CMNPSAYQRT YSMKYFKNSS SAKDNSINTS KHDHRWSRRW QESRR
```

Amino acid sequence for human versican V3 (SEQ ID NO:2).

FIG. 19

THERAPEUTIC COMPOUNDS AND METHODS

CROSS-REFERENCE TO RELATED APPLICATIONS

This application is a continuation under 35 U.S.C. 111(a) from International Application No. PCT/US01/11940 filed Apr. 12, 2001 and published in English as WO 01/79284 A2 on Oct. 25, 2001 which claimed priority from U.S. Provisional Application Serial No. 60/196,805 filed Apr. 13, 2000, which applications are incorporated herein by reference.

GOVERNMENT FUNDING

The invention described herein was made with government support under Grant Number PO1HL-18645 sub-project number 7 awarded by the National Institutes of Health. The United States Government has certain rights in the invention.

BACKGROUND OF THE INVENTION

Versican, the major chondroitin sulfate proteoglycan (CSPG) of the vessel wall (Wight, T. N., The Vascular Extracellular Matrix. In: V., Fuster, R. Ross, and E. J. Topol (eds.), Atherosclerosis and Coronary Artery Disease, pp. 421-440. New York, N.Y.: Raven Press, 1996), is distinguished by a number of important structural features (Margolis, R. U. and Margolis, R. K., Aggrecan-Versican-Neurocan Family of Proteoglycans, Methods Enzymol., 245:105-126, 1994; Zimmermann, D. R. and Ruoslahti, E., Multiple Domains of the Large Fibroblast Proteoglycan, Versican, EMBO J., 8:2975-2981, 1989). The central extended region with attached glycosaminoglycan (GAG) chains confers space filling and viscoelastic properties on the matrix. The chondroitin sulfate chains are highly negatively charged and are believe to contribute anti-adhesive properties to the molecule. This domain is flanked by amino- and carboxy terminal globular domains, through which versican binds to other matrix molecules. The amino-terminal domain is responsible for the binding of versican to the glycosaminoglycan hyaluronan (HA) (LeBaron, R. G., Zimmermann, D. R., and Ruoslahti, E., Hyaluronate Binding Properties of Versican, J. Biol. Chem., 267:10003-10010, 1992). Together, these molecules can form large pericellular coats (Evanko, S. P., Angello, J. C., and Wight, T. N., Formation of Hyaluronan- and Versican-Rich Pericellular Matrix is Required for Proliferation and Migration of Vascular Smooth Muscle Cells, Arterioscler Thromb Vasc Biol., 19: 1004-13, 1999), which are anchored to cells via HA receptors, and which may inhibit the interaction of the cell with other cells or molecules. The carboxy terminal globular domain consists of EGF-like, lectin-like, and compliment-regulatory protein-like domains (Zimmermann, D. R. and Ruoslahti, E., Multiple Domains of the Large Fibroblast Proteoglycan, Versican, EMBO J., 8:2975-2981, 1989). The EGF-like domain has been shown to be pro-proliferative and the lectin-like domain binds tenascin-R and fibulin-1 (Zhang, Y., Cao, L., Yang, B. L., and Yang, B. B., The G3 Domain of Versican Enhances Cell Proliferation via Epidermal Growth Factor-like Motifs, J Biol. Chem., 273:21342-51, 1998; Aspberg, A., Binkert, C., and Ruoslahti, E., The Versican C-type Lectin Domain Recognizes the Adhesion Protein Tenascin-R, Proc. Natl. Acad. Sci. USA, 92:10590-10594, 1995; Aspberg, A., Adam, S., Kostka, G., Timpl, R., and Heinegard, D., Fibulin-1 is a Ligand for the C-type Lectin Domains of Aggrecan and Versican, J. Biol. Chem., 274:20444-20449, 1999).

More recently, versican has been shown to be synthesized as multiple splice variants (Zako, M., Shinomura, T., Ujita, M., Ito, K., and Kimata, K., Expression of PG-M(V3), an Alternatively Spliced form of PG-M without a Chondroitin Sulfate Attachment Region in Mouse and Human Tissues, J. Biol. Chem., 270:3914-3918, 1995; Dours-Zimmermann, M. T. and Zimmermann, D. R., A Novel Glycosaminoglycan Attachment Domain Identified in Two Alternative Splice Variants of Human Versican, J. Biol. Chem., 269:32992-32998, 1994; Ito, K., Shinomura, T., Zako, M., Ujita, M., and Kimata, K., Multiple Forms of Mouse PG-M, a Large Chondroitin Sulfate Proteoglycan Generated by Alternative Splicing, J. Biol. Chem., 270:958-965, 1995). Three of these variants (V0 (Accession No. U16306), V1 (Accession No. X15998), and V2 (Accession No. U26555)), include one or both of the GAG attachment domains and thus differ in the length of the central domain and are predicted to also differ in the number of CS chains attached (Dours-Zimmermann, M. T. and Zimmermann, D. R., A Novel Glycosaminoglycan Attachment Domain Identified in Two Alternative Splice Variants of Human Versican, J. Biol. Chem., 269:32992-32998, 1994; Ito, K., Shinomura, T., Zako, M., Ujita, M., and Kimata, K., Multiple Forms of Mouse PG-M, a Large Chondroitin Sulfate Proteoglycan Generated by Alternative Splicing, J. Biol. Chem., 270:958-965, 1995). A fourth variant, V3, lacks both of the GAG attachment exons and is thus predicted to be a glycoprotein, but not a proteoglycan, and to comprise only the two globular domains (Zako, M., Shinomura, T., Ujita, M., Ito, K., and Kimata, K., Expression of PG-M(V3), an Alternatively Spliced Form of PG-M without a Chondroitin Sulfate Attachment Region in Mouse and Human Tissues, J. Biol. Chem., 270:3914-3918, 1995).

We showed earlier that vascular smooth muscle cells express the originally cloned versican isoform, V1, both in vivo and in vitro, and that versican expression by smooth muscle cells in vitro is regulated by PDGF, TGF-b, and IL-1 (Yao, L. Y., Moody, C., Schonherr, E., Wight, T. N., and Sandell, L. J., Identification of the Proteoglycan Versican in Aorta and Smooth Muscle Cells by DNA Sequence Analysis, In Situ Hybridization and Immunohistochemistry, Matrix Biol., 14:213-225, 1994; Schonherr, E., Jarvelainen, H. T., Sandell, L. J., and Wight, T. N., Effects of Platelet-Derived Growth Factor and Transforming Growth Factor-beta 1 on the Synthesis of a Large Versican-like Chondroitin Sulfate Proteoglycan by Arterial Smooth Muscle Cells, J. Biol. Chem., 266: 17640-17647, 1991; manuscript in preparation). More recently, we have shown that cultured aortic smooth muscle cells can express the V0 and V3 isoforms as well (Lemire, J., Braun, K., Maurel, P., Kaplan, E., Schwartz, S., and Wight, T., Versican/PG-M Isoforms in Vascular Smooth Muscle Cells, Arterioscler. Thromb. Vasc. Biol., 19:1630-1639, 1999). Importantly, however, whereas functions have been demonstrated for V0 and V1 isoforms, no function has been demonstrated for V3. We are interested in the function of versican in vascular tissue, and in particular, in whether the small V3 variant may have a different role.

SUMMARY OF THE INVENTION

The invention provides a viral vector comprising a nucleic acid sequence encoding V3 or a biologically active fragment or variant thereof. In one embodiment, the nucleic acid sequence of the viral vector comprises SEQ ID NO:1, the complement thereof, or a nucleic acid sequence which hybridizes to SEQ ID NO:1 or the complement thereof under stringent or moderate hybridization conditions. In another embodiment, the nucleic acid sequence of the viral vector can encode a polypeptide having SEQ ID NO:2. In one embodiment, the viral vector is a retroviral vector. In one embodiment, the viral vector is LXSN.

The invention also provides a host cell, the genome of which is augmented by a nucleic acid sequence encoding V3 or a biologically active fragment or variant thereof. In one embodiment, the nucleic acid sequence of the host cell comprises SEQ ID NO:1, the complement thereof or a nucleic acid sequence which hybridizes to SEQ ID NO:1 or the complement thereof under stringent or moderate conditions. In another embodiment, the nucleic acid sequence of the host cell encodes the polypeptide having SEQ ID NO:2. In one embodiment, the host cell can be eukaryotic, preferably mammalian, more preferably human.

The invention also provides a method to produce V3 or a biologically active fragment or variant thereof, comprising culturing the host cell of claim 2 so that the host cell expresses V3 or the biologically active fragment or variant thereof.

The invention also provides a pharmaceutical composition comprising V3 or a biologically active fragment or variant thereof, and a pharmaceutically acceptable carrier.

The invention also provides pharmaceutical composition comprising the host cell of claim 2 and a pharmaceutically acceptable carrier.

The invention also provides a method to prevent or treat a pathological condition in a mammal (e.g. a human) wherein V3 is implicated and an increase in V3 activity is indicated comprising administering to the mammal a therapeutically effective amount of an agent. In one embodiment, the agent is a nucleic acid molecule encoding V3, a V3 polypeptide, a biologically active thereof, the host cell of claim 2, an antisense V0 nucleic acid molecule, an antisense V1 nucleic acid molecule, an antisense V2 nucleic acid molecule, or any combination thereof. The agent may be administered topically. In one embodiment, the host cell is contacted with a tissue of the mammal. In another embodiment, the administration of the agent increases the amount of elastic fiber in mammalian tissue, promotes the growth elastic fibers in mammalian blood vessels, increases adhesion of the cells of the mammal, decreases proliferation of mammalian cells, improves the seeding capacity (in vivo and ex vivo) of mammalian cells in a tissue, improves the growth of mammalian cells on a scaffold, or reduces or eliminates wrinkles in mammalian tissue. In another embodiment, the administration of the agent prevents or treats emphysema in a mammal in need of such therapy, prevents lesion formation in mammalian tissue following angioplasty, promotes an increase in the amount of elastic fibers in mammalian cartilage, promotes wound healing in a mammal, or treats or prevents Marfan's syndrome or aortic dissections.

The invention also provides a pharmaceutical composition comprising an effective amount of an agent that increases the expression (amount) or activity of V3 in a mammal, and a pharmaceutically acceptable carrier.

The invention also provides a method to prevent or treat a pathological condition in a mammal (e.g. a human) wherein V3 is implicated and an increase in V3 activity is indicated comprising administering to the mammal a therapeutically effective amount of an agent that increases the expression or activity of V3.

The invention also provides a method to increase the amount of elastic fibers in mammalian tissue comprising contacting the tissue with an effective amount of an agent that increases the expression or activity of V3.

The invention also provides a method to promote the growth elastic fibers in mammalian blood vessels comprising contacting the blood vessels with an effective amount of an agent that increases the expression or activity of V3.

The invention also provides a method to increase adhesion of mammalian cells comprising contacting the cells with an effective amount of an agent that increases the expression or activity of V3.

The invention also provides a method to decrease proliferation of mammalian cells comprising contacting the cells with an effective amount of an agent that increases the expression or activity of V3.

The invention also provides a method to improve the seeding capacity of mammalian cells in a tissue graft comprising contacting the cells with an effective amount of an agent that increases the expression or activity of V3.

The invention also provides a method to improve the growth of mammalian cells on a scaffold comprising contacting the cells with an effective amount of an agent that increases the expression or activity of V3.

The invention also provides a method to reduce or eliminate wrinkles in mammalian tissue comprising contacting the tissue with an effective amount of an agent that increases the expression or activity of V3.

The invention also provides a therapeutic method to prevent or treat emphysema in a mammal in need of such therapy comprising administering to the mammal an effective amount of an agent that increases the expression or activity of V3.

The invention also provides a method to prevent lesion formation in mammalian tissue following angioplasty comprising contacting the tissue with an effective amount of an agent that increases the expression or activity of V3.

The invention also provides a method to promote the growth elastic fibers in mammalian cartilage comprising contacting the cartilage with an effective amount of an agent that increases the expression or activity of V3.

The invention also provides a method to promote wound healing in a mammal comprising administering to the mammal an effective amount of an agent that increases the expression or activity of V3.

The invention also provides a method to treat or prevent Marfan's syndrome or aortic dissections in a mammal comprising administering to the mammal an effective amount of an agent that increases the expression or activity of V3.

The present invention provides a transgenic plant comprising an recombinant DNA segment encoding V3 or variants or biologically fragments thereof, wherein the DNA segment is operably linked to a promoter functional in plant cells. The expression of this DNA segment in the transgenic plant results in expression of V3 in the transgenic plant, e.g., in the seeds or other parts of the plant. This DNA segment is preferably heritable in that it is preferably transmitted through a complete normal sexual cycle of the fertile plant to its progeny and to further generations.

The present invention also provides a method preparing a transgenic plant having V3 content. The method comprises introducing an isolated DNA segment encoding V3 or biologically fragments thereof, wherein the DNA segment is operably linked to a promoter functional in a plant cell, into regenerable cells of a plant, selecting or identifying transformed cells, and regenerating a transgenic plant from said transformed cells wherein V3 or variants, modifications, derivatives, or biologically fragments thereof are expressed in said plant.

The invention further provides a method for expressing V3 and related polypeptides in dicotyledonous plants (dicot plants) and monocotyledonous plants (monocots) generally by introducing such isolated DNA sequences into regenerable cells of the plant, preferably linked to a promoter operable in said cells. The transformed cells are preferably identified or selected, and then regenerated to yield a preferably fertile plant comprising cells that express V3 or variants, modifications, derivatives, or biologically fragments thereof, e.g., in the seeds or other parts of the plant. The introduced DNA is preferably heritable, e.g., it can be passed by a complete sexual cycle to progeny plants.

In one embodiment, the V3-encoding DNA sequences are incorporated into expression cassettes which can also include DNA sequences encoding transit peptides and selectable marker or reporter genes, operably linked to one or more promoters that are functional in cells of the target plant. The promoter can be an inducible or tissue specific promoter. Other transcription or translation regulatory elements, e.g., enhancers or terminators, can also be functionally linked to the DNA segment.

Cells in suspension culture, or as embryos, intact tissues or organs, can be transformed by a wide variety of transformation techniques, such as microprojectile bombardment, electroporation and *A. tumefaciens*-mediated transformation, as are currently available to the art.

The transmission of the DNA can be evaluated at a molecular level, e.g., Southern or Northern blot analysis, PCR-based methodologies, the biochemical or immunological detection of V3, or by phenotypic analyses.

The invention also provides for a method of producing V3 in a host cell, such as a yeast, plant, insect cell, or bacterium, that can be cultured on a commercial scale. The method includes the steps of introducing an expression cassette comprising a DNA segment encoding V3 or variants, modifications, derivatives, or biologically fragments thereof, into a host cell and expressing the DNA segment in the host cell so as to yield V3 or variants, modifications, derivatives, or biologically fragments thereof. An expression cassette preferably includes transcription and translation regulatory elements, e.g., a promoter, functional in host cell, either of eukaryotic or prokaryotic origin. Preferably, the expression cassette is introduced into a prokaryotic cell, such as *E. coli*, or a eukaryotic cell, such as a yeast or insect cell, that is known to be useful for production of recombinant proteins. Culturing the transformed cells can lead to production of V3 and its derivatives, which can be recovered from the cells or from the culture media.

The present invention is directed to the use of polypeptides, polynucleic acids, recombinant cells, related compositions and therapeutic methods for elastic fiber formation. In particular, the invention is directed to the use of versican splice variant V3 polypeptides (SEQ ID NO:2), antibodies against such polypeptides, polynucleic acid sequences (SEQ ID NO:1) encoding the polypeptides and antisense oligonucleotides thereof, recombinant cells and expression cassettes incorporating such polynucleic acid sequences, along with small inhibitor molecules and agents which inhibit operation of the polypeptides and/or polynucleic acid sequences. The invention is as well directed to V3 derivatives, modifications, variations and/or active fragments of the polypeptides and polynucleotides. Preferably the V3 polypeptides or polynucleotides are vertebrate, more preferably the polypeptides or polynucleotides are human. Preferably the variants have at least 60% homology, more preferably at least 70% homology and most preferably at least 90% homology to the polynucleotide or amino acid sequence set forth in SEQ ID NO:1 or SEQ ID NO:2, respectively. The invention is also directed to therapeutic methods of treatment of diseases associated with excessive and insufficient elastic fiber formation.

Antisense polyoligonucleotides are also included within the invention. They have an ability to hybridize with the polynucleic acid sequences thereby altering their expression within organisms.

Another aspect of the invention is an antisense oligonucleotide 8 to 30 nucleotides in length targeted to a 5' untranslated region, a start codon, a coding region, a stop codon or a 3' untranslated region of a V3 polynucleotide, wherein said antisense compound specifically hybridizes and inhibits the expression of V3.

The viral vectors of the invention may be employed in a method for altering the cellular production V3 and thereby altering the amount of elastin fibers. The method includes contacting a host cell with viral vector incorporating a polynucleic acid encoding V3, or a biologically active portion thereof, so as to yield a transformed cell. The nucleic acid sequence is transcribed in the transformed host cell so as to alter the amount of the polypeptide expressed by the transformed cell. If the polynucleic acid sequence is operably linked to a promoter in a sense orientation, the amount of the recombinant polypeptide produced by the transformed host cell is increased relative to the amount of the polypeptide produced by the corresponding untransformed host cell. If the polynucleic acid sequence is in an antisense orientation relative to a promoter, the amount of the polypeptide produced by the transformed host cell is decreased relative to the amount of the polypeptide produced by the corresponding untransformed host cell.

The invention also provides for the use of antibodies which specifically bind to or recognize V0, V1, V2 or V3 polypeptides, variants or fragments thereof, to decrease the level of active V3 in the host cell. Antibodies of the invention include monoclonal antibodies and polyclonal antibodies.

The invention also provides agents that inhibit the activity of V3 polypeptides or reduces the amount of V3 polypeptide in a cell. The inhibitor agents of the invention include small molecule (including organic and inorganic chemicals) and peptide inhibitors of the polypeptides of the invention. These agents may be useful to decrease the amount and formation of elastic fibers.

The invention also provides a method to screen for an agent which inhibits the activity of a V3 polypeptide or decreases the amount (concentration) of V3 polypeptide in a cell. The method involves obtaining cells naturally expressing V3 or host cells transformed with an expression cassette according to the invention, contacting such cells with the agent, and determining whether the agent inhibits the activity of the polypeptide. The inhibitor agents may bind/interact with the binding site of the V3 polypeptide.

The invention also provides agents that increase the activity of V3 polypeptides or increases the amount (concentration) of V3 polypeptide in a cell. These agents may be useful to increase the amount and formation of elastic fibers.

The invention also provides a method to screen for an agent which increases the amount (concentration) or the activity of a V3 polypeptide in a cell. The method involves obtaining cells naturally expressing V3 or host cells transformed with an expression cassette according to the invention, contacting such cells with the agent, and determining whether the agent increase the level or the activity of the polypeptide.

The invention also provides an for isolated polynucleic acid molecules which hybridizes to SEQ ID NO:1, or the complement thereof under stringent or moderate conditions.

The invention also provides method to prevent or treat a pathological condition in a mammal wherein elastin is implicated and a decrease in elastic fiber is indicated comprising administering to the mammal an effective amount of an agent which inhibits V3 amount or level. In one embodiment, the agent is an antibody raised against V3, or fragments thereof, a small molecule inhibitor or an antisense V3 nucleic acid molecule. In another embodiment, the antisense V3 molecule hybridizes with a polynucleic acid encoding V3 and wherein said antisense V3 molecule does not hybridize with a polynucleic acid encoding V0, V1 or V2. In one embodiment the pathological condition is sun damaged skin, desmoplastic reaction in cancer or elastofibroma.

The invention also provides a pharmaceutical composition comprising a polynucleic acid molecule which is complementary to V0, V1, V2, V3, or a biologically active fragment thereof and a pharmaceutically acceptable carrier.

The invention further provides a vector comprising a nucleic acid sequence which is complementary to a nucleic acid sequence encoding V3 or a fragment thereof. In one embodiment the vector is a viral vector.

The invention also provides a biologically active fragment of a V3 polynucleic acid or polypeptide, an antisense V0 nucleic acid molecule, an antisense V1 nucleic acid molecule, an antisense V2 nucleic acid molecule, or any combination thereof for use in medical therapy.

The invention further provides a nucleic acid molecule encoding V3, a V3 polypeptide, a biologically active fragment thereof, an antisense V0 nucleic acid molecule, an antisense V1, nucleic acid molecule, an antisense V2 nucleic acid molecule, or any combination thereof for use in medical therapy, wherein the medical therapy is not treating arterial damage resulting from balloon angioplasty.

The invention provides a nucleic acid molecule encoding V3, a V3 polypeptide, a biologically active fragment thereof, a host cell, the genome of which is augmented by a nucleic acid sequence encoding V3 or a biologically active fragment thereof, an antisense V0 nucleic acid molecule, an antisense V1, nucleic acid molecule, an antisense V2 nucleic acid molecule, or any combination thereof for use in medical therapy, wherein the medical therapy is not treating arterial damage resulting from balloon angioplasty.

The invention further provides the use of an agent to manufacture a medicament for treating a pathological condition wherein V3 is implicated and an increase in V3 activity or amount is indicated in mammal, wherein the pathological condition is not arterial damage resulting from balloon angioplasty.

The invention also provides the use of an agent to manufacture a medicament for treating a pathological condition wherein V3 is implicated and an increase in V3 activity or amount is indicated in mammal, wherein the agent is not a host cell, the genome of which is augmented by a nucleic acid sequence encoding V3.

In one embodiment, the agent for use in manufacture of a medicament for treating a pathological condition wherein V3 is implicated and an increase in V3 activity or amount is indicated in a mammal, is a nucleic acid molecule encoding V3, a V3 polypeptide, a biologically active fragment thereof, a host cell, the genome of which is augmented by a nucleic acid sequence encoding V3 or a biologically active fragment thereof, an antisense V0 nucleic acid molecule, an antisense V1, nucleic acid molecule, an antisense V2 nucleic acid molecule, or any combination thereof.

BRIEF DESCRIPTION OF THE FIGURES

FIG. 9. Cell coats and cell morphologies of LXSN and LV3SN transfected FRSMC as demonstrated by exclusion of fixed red blood cells (RBC). Vector-alone cells exclude RBC from their upper surfaces, signifying a raised profile, and from their margins (arrows), indicating a cell coat. V3 cells show neither feature, consistent with a flattened morphology that allows RBC to settle on their upper surfaces, and with a reduced cell coat that allows RBC to settle immediately adjacent to cell margins.

FIG. 10. Morphology of dense, long-term (3-week) cultures of vector-alone (LXSN) and V3 (LV3SN) transfected FRSMC showing network of elastic fibres (arrows) in the V3 cultures.

FIG. 18. The polynucleotide cDNA sequence (SEQ ID NO:1) for human versican V3 (PG-M(V3)).

FIG. 19. The amino acid sequence (SEQ ID NO:2) for human versican V3 (PG-M(V3)).

DETAILED DESCRIPTION

Figure 1:
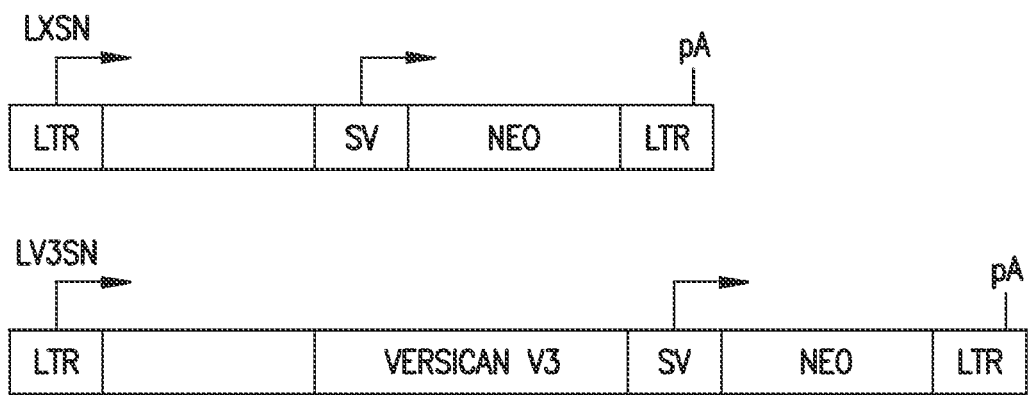
FIG. 1. Schematic depiction of the retroviral vectors LXSN and LV3SN. LTR, retroviral long terminal repeat; NEO, neomycin phosphotransferase; SV, SV40 fragment containing early promoter; pA, polyadenylation site. Arrows indicate transcriptional start sites and direction of transcription.

Applicant has discovered that V3 (a splice variant of versican) and cells expressing V3 promote the formation of elastic fiber in mammalian tissue. Thus, V3 and cells expressing V3 can be used to treat conditions, for example, to promote elastic fiber assembly in vascular reconstructive surgery, to facilitate the building of artificial blood vessels, to promote vascular graft repair, to improve the growth of tissue in vitro (e.g. on a scaffold), to promote vascular healing after atherectomy (e.g. in or on a stent), for treating vessels undergoing aneurysmal changes and dissections created in advanced atherosclerotic lesions, for treating Marfan's syndrome and aortic dissections, for treating emphysema, for treating supravalvular aortic stenosis, for treating Williams syndrome, for treating congenital contractural arachnodactyly (CCA), for reducing wrinkles (e.g. in aging skin), and to promote healing following surgery (e.g. plastic surgery).

As used herein, a therapeutically active fragment or variant of V3 is a portion of V3 that possesses a useful property (e.g. a useful therapeutic property, such as the ability to prevent or treat a pathological condition modulated by the action V3).

Additionally, agents which inhibit V3 transcription, translation or activity, including antisense polynucleotide molecules specific for V3, antibodies raised against V3 or a fragment or variant thereof, or small molecule inhibitors, can be used to treat, prevent or inhibit conditions associated with increased V3 or elastin levels (e.g., excess elastin deposition) or activity, including, but not limited to, sun damaged skin, desmoplastic reaction in cancer, including breast, stomach and colon cancer, and elastofibroma.

Additionally, V3 polynucleotides (sense and antisense) and polypeptides, or biologically active fragments or variants thereof and agents which modulated the level or activity of V3 may be useful in treating Ehlers-Danlos syndrome, pseudoxanthoma elasticum, cutis laxa, lymphangioleiomyomatosis (LAM), or conditions characterized by loose limbs/ligaments.

I. Polypeptides of the Invention

The polypeptides of the present invention include the following: a versican spliced variant V3 (PG-M(V3), herein after V3), any related polypeptides, the amino acid sequence of SEQ ID NO:2, as well as variants, or biologically active fragments thereof.

These polypeptides can be synthesized in vitro, e.g., by the solid phase peptide synthetic method or by recombinant cellular approaches (see above), or by in vitro transcription/translation systems. The synthesis products may be fusion polypeptides, i.e., the polypeptide comprises the polypeptide variant or derivative according to the invention and another peptide or polypeptide, e.g., a His, HA or EE tag. Such methods are described, for example, in U.S. Pat. Nos. 5,595,887; 5,116,750; 5,168,049 and 5,053,133; Olson et al., Peptides, 9, 301, 307 (1988). The solid phase peptide synthetic method is an established and widely used method, which is described in the following references: Stewart et al., Solid Phase Peptide Synthesis, W. H. Freeman Co., San Francisco (1969); Merrifield, J. Am. Chem. Soc., 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., Meth. Enzymol., 287, 233 (1997). These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Derivatives of a polypeptide of the invention can be readily prepared by methods known in the art. See, for example, Advanced Organic Chemistry, J. March, cited infra. For example, amides of the polypeptide of the invention may also be prepared by techniques well known in the art for converting a carboxylic acid group or precursor, to an amide. A preferred method for amide formation at the C-terminal carboxyl group is to enzymatically couple a modified amino acid to the C terminus and convert it to a carboxyamide. For example, use of 2-o-nitrophenylalanine and an exocarboxypeptidase such as carboxypeptidase Y will form the modified alanyl carboxyamide. Photolysis converts the modified alanyl group to an $NH_2$ group such that an unsubstituted carboxyamide is formed. Another method involves cleaving the polypeptide from a solid support with an appropriate amine, or to cleave in the presence of an alcohol, yielding an ester, followed by aminolysis with the desired amine.

Salts of carboxyl groups of a polypeptide of the invention may be prepared in the usual manner by contacting the polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the polypeptide may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N— and O-acylation may be carried out together, if desired.

Formyl-methionine, pyroglutamine and trimethyl-alanine may be substituted at the N-terminal residue of the polypeptide. Other amino-terminal modifications include aminooxypentane modifications (see Simmons et al., Science, 276, 276 (1997)).

The polypeptides of the invention include polypeptides having amino acid substitutions, i.e., variant polypeptides, so long as the polypeptide variant is biologically active. For example, for V3 variants, it is preferred that the variant has at least about 5% of the biological activity of the corresponding non-variant polypeptides, e.g., a polypeptide having SEQ ID NO:2. The variant polypeptides include the substitution of at least one amino acid residue in the polypeptide for another amino acid residue, including substitutions which utilize the D rather than L form, as well as other well known amino acid analogs, e.g., unnatural amino acids such as a, a-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, a-methyl-alanine, para-benzoyl-phenylalanine, phenylglycine, propargylglycine, sarcosine, e-N,N,N-trimethyllysine, e-N-acetyllysine, N-acetylserine, N-formylmethionine, 3-methylhistidine, 5-hydroxylysine, ?-N-methylarginine, and other similar amino acids and imino acids and tert-butylglycine.

Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. Members in each group can be substituted for one another. For example, a group of amino acids having aliphatic side chains is glycine, alanine, valine, leucine, and isoleucine. These may be substituted for one another. A group of amino acids having aliphatic-hydroxyl side chains is serine and threonine. A group of amino acids having amide-containing side chains is asparagine and glutamine. A group of amino acids having aromatic side chains is phenylalanine, tyrosine and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant polypeptide of the invention.

Acid addition salts of the polypeptide or of amino residues of the polypeptide may be prepared by contacting the polypeptide or amine with one or more equivalents of the desired inorganic or organic acid, such as, for example, hydrochloric acid. Esters of carboxyl groups of the peptides may also be prepared by any of the usual methods known in the art.

The polypeptides of the invention may include moieties, e.g., other peptide or polypeptide molecules (fusion polypeptides), such as antibodies or fragments thereof, nucleic acid molecules, sugars, lipids, e.g., cholesterol or other lipid derivatives which may increase membrane solubility, fats, a detectable signal molecule such as a radioisotope, e.g., gamma emitters, small chemicals, metals, salts, synthetic polymers, e.g., polylactide and polyglycolide, and surfactants which preferably are covalently attached or linked to polypeptide of the invention.

The polypeptides of the invention may also be modified in a manner that would increase their stability in vivo, i.e, their resistance to degradation and/or their metabolic half lives. These modifications typically may be chemical alterations of the N— and/or C— terminii and/or alterations of side chain groups by such techniques as esterification, amidation, reduction, protection and the like. Methods to prepare such derivatives are well known to the art. See, for example, Advanced Organic Chemistry, 4th ed., Jerry March, 1992, J. Wiley & Sons, New York.

II. Polynucleic Acids of the Invention

The polynucleic acids of the invention encode at least the polypeptides of the invention or fragments thereof as well as primers, hybridizing sequences and antisense polyoligonucleotides. Full length genes, cDNA sequences, mRNAs and complements thereof are included. In particular, examples of the polynucleic acids include those having sequences as set forth in SEQ ID NO:1, complements thereof and sequences hybridizing to SEQ ID NO:1 and complements thereof.

A. Sources of the Polynucleic Acids of the Invention

Sources of nucleotide sequences from which the present polynucleic acids encoding at least a portion of the polypeptides of the invention, include total or polyA$^+$ RNA from any cellular source such as eukaryotic, preferably mammalian, more preferably human. cDNAs can be derived from these sources by methods known in the art. Other sources of the polynucleic acids of the invention include genomic libraries derived from any eukaryotic cellular source. Moreover, the present polynucleic acids may be prepared in vitro, or by subcloning at least a portion of a DNA segment that encodes a V3 polypeptide.

B. Isolation of the Polynucleic Acids of the Invention

A polynucleic acid encoding a polypeptide of the invention can be identified and isolated using standard methods, as described by Sambrook et al., Molecular Cloning: A Laboratory Manual, Cold Spring Harbor, N.Y. (1989). For example, reverse-transcriptase PCR (RT-PCR) can be employed to isolate and clone V3 cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

The PCR or "Polymerase chain reaction" is a procedure or technique in which amounts of a preselected fragment of polynucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA or poly A+ RNA, bacteriophage or plasmid sequences, and the like. See generally Mullis et al., Cold Spring Harbor Symp. Quant. Biol., 51, 263 (1987); Erlich, ed., PCR Technology, (Stockton Press, New York, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other eukaryotic V3 genes. One primer is prepared which is predicted to anneal to the antisense strand, and another primer prepared which is predicted to anneal to the sense strand, of a DNA molecule which encodes a polypeptide of the invention such as a V3 polypeptide.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone DNAs of the invention, is to screen a cDNA library or genomic library. Screening for DNA fragments that encode all or a portion of a cDNA encoding the polypeptide of the invention can be accomplished by probing the library with a probe which has sequences that are highly conserved between genes believed to be related to the desired polypeptides, e.g., the homolog of V3 from a different species, or by screening of plaques for binding to antibodies that specifically recognize V3. DNA fragments that bind to a probe having sequences which are related to the desired polypeptides, or which are immunoreactive with antibodies to the desired polypeptides, can be subcloned into a suitable vector and sequenced and/or used as probes to identify other DNAs encoding all or a portion of the polypeptides of the invention.

Polynucleotides which are identical or sufficiently identical to a nucleotide sequence contained in SEQ ID NO:1 may be used as hybridization probes for cDNA and genomic DNA or as primers for a nucleic acid amplification (e.g., PCR) reaction, to isolate full-length cDNAs and genomic clones encoding V3 polypeptides and to isolate cDNA and genomic clones of other genes (including genes encoding paralogs, orthologs and homologs from other species) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

A polynucleotide encoding a polypeptide of the present invention, including homologs from other species may be obtained by a process which comprises the steps of screening an appropriate library under stringent hybridization conditions with a labeled probe having the sequence of SEQ ID NO:1 or a fragment thereof, and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1 ×SSC at about 65° C. Thus, the present invention also includes polynucleotides obtainable by screening an appropriate library under stringent hybridization conditions with a labeled probe having the sequence of SEQ ID NO:1 or a fragment thereof.

C. Variants of the Polynucleic Acids of the Invention

Polynucleic acids encoding amino acid sequence variants of a polypeptide of the invention are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of V3.

Oligonucleotide-mediated mutagenesis is a preferred method for preparing amino acid substitution variants of a polypeptide of the invention. This technique is well known in the art as described by Adelman et al., DNA, 2, 183 (1983). Briefly, V3 DNA is altered by hybridizing an oligonucleotide encoding the desired mutation to a DNA template, where the template is the single-stranded form of a plasmid or bacteriophage containing the unaltered or native DNA sequence encoding the desired polypeptide, or a portion thereof. After hybridization, a DNA polymerase is used to synthesize an entire second complementary strand of the template that will thus incorporate the oligonucleotide primer, and will code for the selected alteration in the desired DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., Proc. Natl. Acad. Sci. U.S.A., 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., Meth. Enzymol., 153, 3 (1987). Thus, the DNA that is to be mutated may be inserted into one of these vectors to generate single-stranded template. Production of the single-stranded template is described in Sections 4.21-4.41 of Sambrook et al., Molecular Cloning: A Laboratory Manual (Cold Spring Harbor Laboratory Press, N.Y. 1989). Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the variant form of the polypeptide of the invention, and the other strand (the original template) encodes the native, unaltered sequence of the polypeptide. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM 101.

For example, a preferred embodiment of the invention is a DNA molecule encoding V3 having SEQ ID NO:2, wherein the nucleic acid molecule comprises SEQ ID NO:1, or fragments thereof, or variants of SEQ ID NO:1, having nucleotide substitutions which are "silent". That is, when silent nucleotide substitutions are present in a codon, the same amino acid is encoded as without the substitutions. For example, valine is encoded by the codon GTT, GTC, GTA and GTG. A change in the third nucleotide in a codon for valine, will still result in valine at that position. Other "silent" nucleotide substitutions in SEQ ID NO:1 which can encode V3 having SEQ ID NO:2 can be ascertained by reference to page D1 In Appendix D in Sambrook et al., Molecular Cloning: A Laboratory Manual (1989). Nucleotide substitutions can be introduced into DNA segments by methods well known to the art, for example, Sambrook et al., supra. Likewise, nucleic acid molecules encoding mammalian, preferably human, V3 polypeptides may be modified in a similar manner. Moreover the polynucleic acids of the invention may be modified in a similar manner so as to result in polypeptides that have deletions or additions.

D. Antisense Molecules of the Invention

The nucleotide sequence and chemical structure of an antisense polyoligonucleotide according to the invention can be varied, so long as the polyoligonucleotide retains its ability to inhibit expression of the polypeptide of the invention. Known such techniques involve the use of antisense sequences, either internally generated or externally administered (See, for example, O'Connor, J Neurochem. (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., Nucleic Acids Res. (1979) 6:3073; Cooney et al., Science (1988) 241:456; Dervan et al., Science (1991) 251:1360). These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesized with these or other modified backbones also form part of the present invention.

The present invention employs oligomeric antisense compounds/agents, particularly oligonucleotides, for use in modulating the function of nucleic acid molecules encoding versican splice variants, preferably V0, V1, V2 or V3 polypeptides, ultimately modulating the amount V0, V1, V2 or V3 protein produced. This is accomplished by providing antisense compounds which specifically hybridize with one or more nucleic acids encoding V0, V1, V2 or V3 polypeptide. As used herein, the terms "target nucleic acid" and "nucleic acid encoding V0, V1, V2 or V3" encompass DNA encoding V0, V1, V2 or V3, respectively, polypeptide, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of V0, V1, V2 or V3 polynucleic acids and polypeptides. In the context of the present invention, "modulation" (alteration) means either an increase (stimulation) or a decrease (inhibition) in the expression of a gene.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state. In the present invention, the target is a nucleic acid molecule encoding V3 polypeptide, specifically SEQ ID NO:2. The target nucleic acid molecule may also be a nucleic acid molecule encoding V0, V1 or V2 polypeptide. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding V0, V1, V2 or V3 polypeptide, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e. from about 8 to about 30 linked nucleosides). Particularly preferred antisense compounds are antisense oligonucleotides, even more preferably those comprising from about 12 to about 25 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative Unite States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262. Further teaching of PNA compounds can be found in Nielsen et al., Science, 1991, 254, 1497-1500.

Modified oligonucleotides may also contain one or more substituted sugar moieties. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-

1.2.degree. C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,750,692 and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the present invention can be utilized for diagnostics, therapeutics, prophylaxis and as research reagents and kits. For therapeutics, in an animal, preferably a human, suspected of having a disease or disorder which can be treated by modulating the expression of a V3 polypeptide or polynucleotide is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

III. Preparation

A. Polynucleic Acids

1. Chimeric Expression Cassettes

Once a DNA sequence encoding V0, V1, V2 or V3, antisense molecules, variants, or biologically fragments thereof is obtained and amplified, it is operably combined with a promoter and, optionally, with other elements to form an expression cassette. To prepare expression cassettes for transformation, the recombinant or selected polynucleic acid sequence or segment may be circular or linear, double-stranded or single-stranded. A DNA sequence which encodes a polypeptide of the invention may be inserted into a cassette in either orientation.

Generally, the polynucleic acid sequence or segment is in the form of chimeric DNA, such as plasmid DNA, that can also contain coding regions flanked by control sequences which promote the expression of the selected DNA present in the resultant cell line.

Aside from nucleic acid sequences that serve as transcription units for the polypeptides of the invention, a portion of the nucleic acid molecule may include control sequences. These may be untranscribed, serving a regulatory or a structural function. For example, most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. The DNA may itself include a promoter that is active in host cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention. Other useful promoters include the bacteriophage SP6, T3, and T7 promoters. It is contemplated that other promoters useful in the practice of the invention are known to those of skill in the art.

Additionally, promoter sequences are known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired.

The promoter in an expression cassette of the invention can provide for expression of V3 from a DNA sequence encoding V3. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the gene with a promoter that provides tissue specific expression or developmentally regulated gene expression.

Useful promoters for expression in plant host cells include the CaMV 35S promoter (Odell et al., Nature, 313, 810 (1985)), the CaMV 19S (Lawton et al., Plant Mol. Biol., 9, 31F (1987)), nos (Ebert et al., PNAS USA, 84, 5745 (1987)), Adh (Walker et al., PNAS USA, 84, 6624 (1987)), sucrose synthase (Yang et al., PNAS USA, 87, 4144 (1990)), napin, actin (Wang et al., Mol. Cell. Biol., 12, 3399 (1992)), cab (Sullivan et al., Mol. Gen. Genet., 215, 431 (1989)), PEPCase promoter (Hudspeth et al., Plant Mol. Biol., 12, 579 (1989)), the 7S-alpha'-conglycinin promoter (Beachy et al., EMBO J, 4, 3047 (1985)) or those associated with the R gene complex (Chandler et al., The Plant Cell, 1, 1175 (1989)).

Other sequences functional in the host cells, such as introns, enhancers, polyadenylation sequences and the like, may also be a part of the DNA. Such elements may or may not be necessary for the function of the DNA, but may provide improved expression of the DNA by affecting transcription, stability of the mRNA, or the like. As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art. Such elements may be included in the DNA as desired to obtain the optimal performance of the transforming DNA in the cell. All of these various sequences may be operably linked although they are not necessarily directly linked.

Additionally, expression cassettes may be constructed and employed to provide targeting of the gene product to an intracellular compartment within plant cells or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences may increase the accumulation of gene product.

The DNA to be introduced into the cells may also generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of E. coli, the beta-glucuronidase gene (GUS) of the uidA locus of E. coli, and the luciferase gene from firefly Photinus pyralis. Expression of the reporter gene is assayed at a suitable time after the DNA has been introduced into the recipient cells.

Plasmid vectors can include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Viral vectors are also useful for expression of V0, V1, V2, or V3 molecules (polynucleic acid or polypeptide) in eukaryotic and prokaryotic cells. Viral vectors useful in the present invention include, but are not limited to, adenoviral, AAV, LXSN, or baculoviral vectors.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA582. This binary Ti vector can be replicated in prokaryotic bacteria such as *E. coli* and *Agrobacterium*. The *Agrobacterium* plasmid vectors can also be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells. See, for example, Glassman et al., U.S. Pat. No. 5,258,300.

The general methods for constructing recombinant DNA which can transform host cells are well known to those skilled in the art, and the same compositions and methods of construction may be utilized to produce the DNA useful herein. For example, J. Sambrook et al., Molecular Cloning: A Laboratory Manual, Cold Spring Harbor Laboratory, NY (1989), provides suitable methods of construction.

2. Transformation into Host Cells

The recombinant DNA can be readily introduced into the host cells, e.g., mammalian, bacterial, plant, yeast or insect cells (e.g., baculoviral expression systems) by transfection with an expression vector incorporating the polynucleic acids of the invention by any procedure useful for the introduction into a particular cell, e.g., physical or biological methods, to yield a transformed cell having the recombinant DNA stably integrated into its genome, so that the DNA molecules, polynucleic acids, sequences, or segments, of the present invention are expressed by the host cell.

Physical methods to introduce a DNA into a host cell include calcium phosphate precipitation, lipofection, particle bombardment, microinjection, electroporation, and the like. Methods of transformation especially effective for dicots, include, but are not limited to, microprojectile bombardment of immature embryos (U.S. Pat. No. 5,990,390) or Type II embryogenic callus cells as described by W. J. Gordon-Kamm et al. (Plant Cell, 2, 603 (1990)), M. E. Fromm et al. (Bio/Technology, 8, 833 (1990)) and D. A. Walters et al. (Plant Molecular Biology, 18, 189 (1992)), or by electroporation of type I embryogenic calluses described by D'Halluin et al. (The Plant Cell, 4, 1495 (1992)), or by Krzyzek (U.S. Pat. No. 5,384,253, issued Jan. 24, 1995). Transformation of plant cells by vortexing with DNA-coated tungsten whiskers (Coffee et al., U.S. Pat. No. 5,302,523, issued Apr. 12, 1994) and transformation by exposure of cells to DNA-containing liposomes can also be used.

Biological methods to introduce the DNA of interest into a host cell include the use of DNA and RNA viral vectors. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding a polypeptide of the invention or its complement, which host cell may or may not express significant levels of autologous or "native" V3 polypeptide.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; and "biochemical" assays, such as detecting the presence or absence of a particular polypeptide, e.g., by immunological means (ELISAs and Western blots).

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and demonstrate the presence or absence of an RNA species.

Southern blotting and PCR may be used to detect the preselected DNA segment in question. Expression of the DNA segment may be evaluated by specifically identifying the peptide products of the introduced DNA sequences or evaluating the phenotypic changes brought about by the expression of the introduced DNA segment in the host cell.

IV. Pharmaceutical Compositions

Pharmaceutical compositions of the polynucleic acids, polypeptides, antibodies, antisense oligonucleotides or agents of the invention are particularly useful for modulation of V3 and/or elastin levels/activity in mammals. An effective amount of an agent within the pharmaceutical compositions of the invention may be administered to a mammal for a time and under conditions sufficient to modulate the activity/levels of V3 and/or elastin.

In cases where V3 or an agent is sufficiently basic or acidic to form stable nontoxic acid or base salts, administration of the agents as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, and ascorbate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

A host cell or other agent of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, an agent may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food (see section below on expression of V3 in plants) of the patient's diet. For oral therapeutic administration, the active agent may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of active agent in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active agent, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active agent may be incorporated into sustained-release preparations and devices.

A host cell or other agent of the invention may also be administered intravenously or intraperitoneally by infusion or injection. Solutions of the agents or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, a host cell or other agent of the invention may be applied in pure form. However, it will generally be desirable to administer them to skin or tissue as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present agents can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a host cell or other agent of the invention are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

According to the invention, V3 or antisense V0, V1, V2 or V3 molecule production in a given tissue can also be achieved by cell mediated gene transfer.

V. Therapeutic Method

The invention includes the treatment of disease resulting from excessive or insufficient V3 or elastin levels or activity in mammals by administering a pharmaceutical composition containing a pharmaceutically effective amount of an agent of the invention. A method for treating abnormal elastin activity or levels in a mammal is contemplated in which an appropriate agent is introduced into a cell in such a manner that the agent is expressed intracellularly. Such expression may be extrachromosomal in a cell or occur following integration into the genome of the cell. Where the appropriate agent, such as a polypeptide, inhibitor peptide, complement or antisense oligonucleotide, is introduced into the cell by a polynucleic acid, the polynucleic acid may be carried to the cell and transferred into the cell by a transfection vector such as a virus. Moreover, administration of sense or antisense polynucleic acids of the invention may be accomplished through the introduction of cells transformed with an expression cassette including the polynucleic acid (see, for example WO 93/02556) or the administration of the polynucleic acid (see, for example, Felgner et al., U.S. Pat. No., 5,580,859, Pardoll et al., Immunity, 2, 165 (1995); Stevenson et al., Immunol Rev., 145, 211 (1995); Molling, J. Mol. Med., 75, 242 (1997); Donnelly et al., Ann. N.Y. Acad. Sci., 772, 40 (1995); Yang et al., Mol. Med. Today, 2, 476 (1996); Abdallah et al., Biol. Cell, 85, 1 (1995); U.S. Pat. No., 6,020,318). Pharmaceutical formulations, dosages and routes of administration for polynucleic acids are generally disclosed, for example, in Felgner et al. and Szyf et al., supra.

Furthermore, the invention includes treating disease resulting from excessive V3 and/or elastin activity or levels in mammals by administering a pharmaceutical composition containing a pharmaceutically effective amount of an agent of the invention, including a small molecule inhibitor, an antibody, a peptide inhibitor agent or a polynucleic acid which is the complement (antisense) of a polynucleic acid encoding a polypeptide of the invention. For example, a method for treating abnormal elastin activity or levels is contemplated in which a small molecule inhibitor, antibody or an agent which inhibits the activity of a V3 polypeptide, is administered as a pharmaceutical composition in an effective amount to treat such diseases.

For topical administration, a host cell of the invention or an agent may be administered to skin or tissue as compositions or formulations, in combination with a dermatologically acceptable carrier, which may be a solid or a liquid, or alternatively, they may be administered in pure form.

VI. Screen for Agents which Modulate V3 Activity or Levels

Agents according to the invention include antibodies, small molecules, polynucleic acids and polypeptides. The ability to inhibit or increase the activity and/or level of V3 can be determined by applying a pharmaceutical composition containing the agent to a culture containing transformed host cells described above. The amount/level of elastin and/or V3 polypeptide and/or polynucleotide production in the transformed host cells can be determined by known methods.

It has been observed that an increase in V3 production results in an alteration of the cell's shape. Therefore, the ability to inhibit or increase the activity and/or level of V3 can be determined by applying a pharmaceutical composition containing the agent to a culture containing transformed host cells described above. The qualitative effect of which can be determined by the comparison of the cell shape of treated and untreated cells. The amount/level of elastin and/or V0, V1, V2 or V3 polynucleotide and/or polypeptide produced in the cell can then be determined by known methods.

VII. Antibodies of the Invention

The antibodies of the invention are prepared by use of standard techniques. To prepare polyclonal antibodies or "antisera," an animal is inoculated with an antigen that is an isolated and purified polypeptide of the invention, and immunoglobulins are recovered from a fluid, such as blood serum, that contains the immunoglobulins, after the animal has had an immune response. For inoculation, the antigen is preferably bound to a carrier peptide and emulsified using a biologically suitable emulsifying agent, such as Freud's incomplete adjuvant. A variety of mammalian or avian host organisms may be used to prepare polyclonal antibodies.

Following immunization, Ig is purified from the immunized bird or mammal, e.g., goat, rabbit, mouse, rat, or donkey and the like. For certain applications, it is preferable to obtain a composition in which the antibodies are essentially free of antibodies that do not react with the immunogen. This composition is composed virtually entirely of the high titer, monospecific, purified polyclonal antibodies to the antigen. Antibodies can be purified by affinity chromatography. Purification of antibodies by affinity chromatography is generally known to those skilled in the art (see, for example, U.S. Pat. No. 4,533,630). Briefly, the purified antibody is contacted with the purified polypeptide, or a peptide thereof, bound to a solid support for a sufficient time and under appropriate conditions for the antibody to bind to the polypeptide or peptide. Such time and conditions are readily determinable by those skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the F(ab) fragment, scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments which retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

The antibodies of the invention are useful for detecting or determining the presence or amount of a polypeptide of the invention in a sample. The antibodies are contacted with the sample for a period of time and under conditions sufficient for antibodies to bind to the polypeptide so as to form a binary complex between at least a portion of said antibodies and said polypeptide. The presence of the complex may then be detected by a sandwich assay, ELISA assay, colorometric protein assay, radiolabeling assay or other known techniques for antibody-antigen detection. Such times, conditions and reaction media can be readily determined by persons skilled in the art.

For example, the cells are lysed to yield an extract which comprises cellular proteins. Alternatively, intact cells are permeabilized in a manner which permits macromolecules, i.e., antibodies, to enter the cell. The antibodies of the invention are then incubated with the protein extract, e.g., in a Western blot, or permeabilized cells, e.g., prior to flow cytometry, so as to form a complex. The presence or amount of the complex is then determined or detected.

The antibodies of the invention may also be coupled to an insoluble or soluble substrate. Soluble substrates include proteins such as bovine serum albumin. Preferably, the antibodies are bound to an insoluble substrate, i.e., a solid support. The antibodies are bound to the support in an amount and manner that allows the antibodies to bind the polypeptide (ligand). The amount of the antibodies used relative to a given substrate depends upon the particular antibody being used, the particular substrate, and the binding efficiency of the antibody to the ligand. The antibodies may be bound to the substrate in any suitable manner. Covalent, noncovalent, or ionic binding may be used. Covalent bonding can be accomplished by attaching the antibodies to reactive groups on the substrate directly or through a linking moiety.

The solid support may be any insoluble material to which the antibodies can be bound and which may be conveniently used in an assay of the invention. Such solid supports include permeable and semipermeable membranes, glass beads, plastic beads, latex beads, plastic microtiter wells or tubes, agarose or dextran particles, sepharose, and diatomaceous earth. Alternatively, the antibodies may be bound to any porous or liquid permeable material, such as a fibrous (paper, felt etc.) strip or sheet, or a screen or net. A binder may be used as long as it does not interfere with the ability of the antibodies to bind the ligands.

VIII. Plants of the Invention

In order to produce V3 in the plant, the DNA sequence encoding V3 must be introduced into the plant cells and these transformed cells identified, either directly or indirectly. The gene should also be stably incorporated into the plant cell genome. The transcriptional signals of the gene should be recognized by and be functional in the plant cells. That is, the gene should be transcribed into messenger RNA, and the mRNA should be stable in the plant nucleus and be transported intact to the cytoplasm for translation. The gene should have appropriate translational signals to be recognized and properly translated by plant cell ribosomes. The polypeptide gene product should escape proteolytic attack in the cytoplasm.

A. Plant Regeneration and Production of Seed

Transformed embryogenic calli, meristemate tissue, embryos, leaf discs and the like can be used to generate transgenic plants that exhibit stable inheritance of the V3 gene. Plant cell lines exhibiting satisfactory levels of V3 are put through a plant regeneration protocol to obtain mature plants and seeds expressing the traits by methods well known in the art (for example, see U.S. Pat. Nos. 5,990,390, 5,489,520; and Laursen et al., Plant Mol. Biol., 24, 51 (1994)). The plant regeneration protocol allows the development of somatic embryos and the subsequent growth of roots and shoots. To determine that V3 is expressed in differentiated organs of the plant, and not solely in undifferentiated cell culture, regenerated plants can be assayed for the levels of V3 present in various portions of the plant relative to regenerated, non-transformed plants. Transgenic plants and seeds can be generated from transformed cells and tissues showing V3 content using standard methods.

Mature plants are then obtained from cell lines that are known to express V3. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The V3 is genetically characterized by evaluating the segregation of the V3 in first and later generation progeny. The heritability and expression in plants of traits selected in tissue culture are of particular importance if the traits are to be commercially useful.

The commercial value of V3 producing soybeans, cereals and other plants is greatest if many different hybrid combinations are available for sale. The farmer typically grows more than one kind of hybrid based on such differences as maturity, standability or other agronomic traits. Additionally, hybrids adapted to one part of the country are not adapted to another part because of differences in such traits as maturity, disease, and insect resistance. Because of this, it is preferable to breed V3 production into a large number of parental lines so that many hybrid combinations can be produced.

A conversion process (backcrossing) is carried out by crossing the original producing line to normal elite lines and crossing the progeny back to the normal parent. The progeny from this cross will segregate such that some plants carry the gene responsible for production whereas some do not. Plants carrying such genes will be crossed again to the normal parent resulting in progeny which segregate for production and normal production once more. This is repeated until the original normal parent has been converted to an producing line, yet possesses all other important attributes as originally found in the normal parent. A separate backcrossing program is implemented for every elite line that is to be converted to V3 producing line.

Subsequent to the backcrossing, the new producing lines and the appropriate combinations of lines which make good commercial hybrids are evaluated for production as well as a battery of important agronomic traits. Producer lines and hybrids are produced which are true to type of the original normal lines and hybrids. This requires evaluation under a range of environmental conditions where the lines or hybrids will generally be grown commercially. For production of V3 soybeans, it may be necessary that both parents of the hybrid seed be homozygous for the V3 character. Parental lines of hybrids that perform satisfactorily are increased and used for hybrid production using standard hybrid seed production practices.

Transgenic plants may find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from soybean cells to cells of other species, e.g., by protoplast fusion.

B. Plants

Plants for use of the invention include dicots and monocots, including but not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Ca-

*mellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers; duckweed (Lemna, see WO 00/07210, which includes members of the family Lemnaceae.)

Definitions for the Invention

Antibodies: This term includes polyclonal and monoclonal antibodies, chimeric, single-chain, and humanized antibodies, as well as Fab fragments, including the products of a Fab or other immunoglobulin expression library.

Biologically active: A polypeptide or fragment that is biologically active means that the polypeptide elicits a biological response from a cell or organism. With reference to antisense sequences, a "biologically active portion" means that the portion inhibits the expression of V3, e.g., endogenous (native) human V3 in human cells, or recombinant human V3 in a transfected cell.

As used herein, a DNA or polypeptide molecule, sequence or fragment of the invention preferably is biologically active. A biologically active DNA or polypeptide molecule of the invention has at least about 1%, more preferably at least about 10%, and more preferably at least about 50%, of the activity of a DNA or polypeptide molecule comprising SEQ ID NO:1 or SEQ ID NO:2, respectively.

The activity of a nucleic acid or polypeptide molecule of the invention can be measured by methods well known to the art. For example, the presence of the DNA molecule in a recombinant nucleic acid molecule in a host cell results in increased abundance of the recombinant molecule in those cells relative to corresponding cells having a recombinant nucleic acid molecule lacking a DNA molecule of the invention. The biological activity of a V3 polypeptide includes the ability to promote an increase in the amount of elastic fiber in mammalian tissue, promote an increase in the amount of elastic fiber in mammalian blood vessels, increase adhesion of mammalian cells, decrease proliferation of mammalian cells, improve the seeding capacity of mammnalian cells in a tissue graft, improve the growth of mammalian cells on a scaffold, reduce or eliminate wrinkles, prevent or treat emphysema, prevent lesion formation in mammalian tissue following angioplasty, promote the amount of elastic fiber in mammalian cartilage, promote wound healing, treat or prevent Marfan's syndrome, or prevent or treat a pathological condition.

Cell line or host cell: This term includes well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources.

Chimeric: "Chimeric" means that a vector includes DNA from at least two different species, or includes DNA from the same species, which is linked or associated in a manner which does not occur in the "native" or wild type of the species.

Cloning vector: This term means a plasmid, viral or phage DNA or other DNA sequence which is able to replicate autonomously in a host cell. The vector is characterized by one or a small number of restriction endonuclease recognition sites at which such DNA sequences may be cut in a determinable fashion without loss of an essential biological function of the vector, and into which a DNA fragment may be inserted in order to bring about its replication and cloning. The cloning vector may further contain a marker suitable for use in the identification of cells transformed with the cloning vector. Markers, for example, provide tetracycline resistance or ampicillin resistance.

Complementary DNA (cDNA): A "complementary DNA," or "cDNA" gene includes recombinant genes synthesized by reverse transcription of mRNA and from which intervening sequences (introns) have been removed.

Control sequences: This term means DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Derivative: The term "derivative" includes the "chemical derivatives" of the molecule. As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in Remington's Pharmaceutical Sciences (1980) and will be apparent to those of ordinary skill in the art.

Expression: Expression is the process by which a polypeptide is produced from a structural gene. The process involves transcription of the gene into mRNA and the translation of such mRNA into polypeptide(s).

Expression vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Fragment: A "fragment" of a molecule is meant to refer to any polypeptide or polynucleotide subset of that molecule.

Homologous/Nonhomologous: Two nucleic acid molecules are considered to be "homologous" if their nucleotide sequences share a similarity of greater than 40%, as determined by HASH-coding algorithms (Wilber, W. J. and Lipman, D. J., Proc. Natl. Acad. Sci., 80, 726-730 (1983)). Two nucleic acid molecules are considered to be "nonhomologous" if their nucleotide sequences share a similarity of less than 40%.

Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M. Stockton Press, New York, 1991). While there exist a number of methods to measure identity between two polynucleotide or polypeptide sequences, the term "identity" is well known to skilled artisans (Carillo, H. and Lipton, D., SIAM Applied Math., 48, 1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. and Lipton, D., SIAM J. Applied Math., 48, 1073 (1988). Methods to determine identity and similarity are codified in computer programs. Preferred computer program methods to determine identity and similarity between two sequences include, but are not limited to, GCS program package (Devereux, J., et al., Nucleic Acids Research, 12(1), 387 (1984)), BLASTP, BLASTN, FASTA (Altschul, S. F. et al., J. Mol. Biol., 215, 403 (1990)).

Therefore, as used herein, the term "identity" represents a comparison between a test and reference polynucleic acid or polypeptide. More specifically, a test polynucleic acid or polypeptide is defined as any molecule that is 90% or more identical to a reference polynucleic acid or polypeptide, respectively. As used herein, the term "90% or more" refers to percent identities from 90 to 99.99 relative to the reference molecule. Identity at a level of 90% or more is indicative of the fact that, assuming for exemplification purposes a test and reference polypeptide length of 100 units, that no more than 10% (i.e., 10 out of 100) units in the test polypeptide differ from that of the reference polypeptide. Such differences may be represented as point mutations randomly distributed over the entire length of the sequence or they may be clustered in one or more locations of varying length up to the maximum allowable 10 unit difference. Differences are defined as nucleotide substitutions, deletions or additions of sequence. These differences may be located at any position in the sequence, including but not limited to the C— and N-termini regions, epitopal regions, 5' end, 3' end, coding and non-coding sequences.

Modified nucleotides: This term includes nucleotides, polynucleotides and oligonucleotides with modified or substituted sugar groups and the like.

Oligonucleotide linkages: This term includes oligonucleotide linkages such as phosphorothioate, phosphorodithioate, phosphoroselenoate, phosphorodeselenoate, phosphoranilothioate, phosphoraniladate, phosphoroamidate, and the like. An oligonucleotide can include a label for detection, if desired.

Oligonucleotide or primer: These terms include naturally occurring, and modified nucleotides linked together by naturally occurring, and non-naturally occurring oligonucleotide linkages. Oligonucleotides are a polynucleotide subset with 200 or fewer bases in length. Preferably, oligonucleotides are about 10 to about 60 bases in length and most preferably from about 12 to 20 to about 40 bases in length. Oligonucleotides are usually single stranded, e.g., for probes, although oligonucleotides may be double stranded, e.g., for use in the construction of a variant. Oligonucleotides can be either sense or antisense oligonucleotides.

Operably linked: This term means that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers may be used in accord with conventional practice.

Pharmaceutically acceptable carrier: This term includes any and all solvents, dispersion media, excipients, fillers, inert solids, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in the pharmaceutical compositions is contemplated. Supplemental active ingredients can also be incorporated into the compositions.

Polynucleic acid: This term generally refers to any polyribonucleotide or polydeoxyribonucleotide, which may be unmodified RNA or DNA or modified RNA or DNA. "Polynucleic acids" include, without limitation, single- and double-stranded DNA, DNA that is a mixture of single- and double-stranded regions, single- and double-stranded RNA, and RNA that is a mixture of single- and double-stranded regions, hybrid molecules including DNA and RNA that may be single-stranded or, more typically, double-stranded or a mixture of single- and double-stranded regions. In addition, "polynucleic acid" refers to triple-stranded regions of RNA or DNA or both RNA and DNA. The term polynucleic acid also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA. Thus, "polynucleic acid" embraces chemically, enzymatically or metabolically modified forms of polynucleotides as typically found in nature, as well as the chemical forms of DNA and RNA characteristic of viruses and cells. "Polynucleic acid" also embraces relatively short polynucleotides, often referred to as oligonucleotides.

Hybridization: This term means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense agent need not be 100% complementary to that of its target nucleic acid to be specifically hybridizable. An antisense compound/agent is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Stringent and Moderate: "Stringent hybridization conditions" and "stringent hybridization wash conditions" in the context of nucleic acid hybridization experiments such as Southern and Northern hybridizations and library screening are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC was at 65° C. for 15 minutes (see, Sambrook, infra, for a description of SSC buffer). Often, a high stringency wash is preceded by a low stringency wash to remove backgrounds probe signal. An example medium stringency was for duplex of, e.g., more than 100 nucleotides, is 1 ×SSC at 45° C. for 15 minutes. An example of low stringency for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 and 8.3, and the temperature is typically at least about 30° C. and at least 60° C. for long probes (e.g., >50 nucleotides). Stringent conditions may also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1 ×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1 to 2×SSC (20×SSC=3.0M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that maybe used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPo$_4$, 1 mM EDTA at 50° C. with washing in 2×SSC, 0.1% SDS at 50° C., more desirably in 7% SDS, 0.5 M NaPO$_4$, 1 mM EDTA at 50° C. with washing in 1×SSC, 0.1% SDS at 50° C., more desirably still in 7% SDS, 0.5 M NaPO$_4$, 1 mM EDTA at 50° C. with washing in 0.5×SSC, 0.1% SDS at 50° C., preferably in 7% SDS, 0.5 M NaPO$_4$, 1 mM EDTA at 50° C. with washing in 0.1×SSC, 0.1% SDS at 50° C., more preferably in 7% SDS, 0.5 M NaPO$_4$, 1 mM EDTA at 50° C. with washing in 0.1×SS, 0.1% SDS at 65° C.

Polypeptide: This term refers to any peptide or protein having two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

Polypeptides include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitization, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid of lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, CPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins-Structure and Molecular Properties, 2nd Ed., T. E. Creighton, W. H., Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 193; Seifter et al., "Analysis for protein modifications and nonprotein cofactors," Methods in Enzymol, 182: 626-646 (1990) and Rattan et al., "Protein Synthesis: Posttranslational Modifications and Aging," Ann. N.Y. Acad. Sci., 663, 48-62 (1992).

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Substantially similar: A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

Variant or Variation: As used herein, V3 molecules are intended to encompass polynucleic acid and polypeptide molecules with substitutions, such that the variant polynucleic acid or polypeptide differs in sequence from a wild type V3 polynucleic acid molecule or polypeptide respectively, but retains biological activity. Changes in the nucleotide sequence of the variant may or may not alter the amino acid sequence of a polypeptide encoded by the wild type V3 polynucleic acid. Nucleotide changes may result in amino acid substitutions, additions, deletions, fusions and truncations in the polypeptide encoded by the wild type V3 sequence.

A typical variant of a polypeptide differs in amino acid sequence from a wild type V3 polypeptide. Generally, differences are limited so that the sequences of the wild type V3 polypeptide and the variant are substantially similar, and, in many regions, have identity. A variant and wild type polypeptide may differ in amino acid sequence by one or more substitutions, additions, deletions in any combination. A substituted or inserted amino acid residue may or may not be one encoded by the genetic code, e.g., a D-amino acid or one other than an alpha amino acid, such as 3-amino propionic acid, or taurine. A variant of a polynucleotide or polypeptide may be naturally occurring such as an allelic variant, or it may be a variant that is not known to occur naturally. Non-naturally occurring variants of polynucleotides and polypeptides may be made by mutagenesis techniques or by direct synthesis.

A variant of SEQ ID NO:2 is a polypeptide that has at least about 80%, preferably at least about 90%, but less than 100%, contiguous amino acid sequence homology or identity to the amino acid sequence corresponding to SEQ ID NO:2 and is biologically active.

A variant V3 polypeptide of the invention may include amino acid residues not present in SEQ ID NO:2, e.g., amino acid substitutions, and amino and/or carboxy termini, or internal deletions or insertions, of amino acid residues relative to SEQ ID NO:2. Variant polypeptides of the invention may include polypeptides having at least one D-amino acid, as well as moieties other than amino acid residues that correspond to SEQ ID NO:2, such as amino acid residues that form a part of a fusion protein, nucleic acid molecules or targeting moieties such as antibodies or fragments thereof.

Preparation and identification of such variants are described herein above.

The invention is illustrated by the following non-limiting Examples.

EXAMPLE 1

Materials and Methods

Retroviral transfection: The rat V3 cDNA, rVe (Lemire, 1999, #448), had an upstream sequence of 18T's which we believed to be an artifact of its cloning into the vector in the reverse direction. To remove this sequence, the V3 sequence was prepared as follows, using standard molecular biology protocols (Sambrook, J., Fritsch, E. F., and Maniatis, T., Molecular Cloning: A Laboratory Manual, Second edition, Cold Spring Harbor, N.Y : Cold Spring Harbor Laboratory, 1989). The rVe cDNA in pBSM 13+ was linearized with Nar I, at position −188 of the 5 ' untranslated region. The overhanging ends were filled-in with Klenow fragment and Bam HI linkers were attached. After digestion with Bam HI, which cut both the linker and a sequence in the multicloning site at the other end of the versican sequence, the V3 sequence was inserted into the Barn HI site of the retroviral vector LXSN (courtesy of Dr. A. D. Miller, Fred Hutchinson Cancer Research Center, Seattle, Wash.; Miller, A. D. and Rosman, G. J., Improved Retroviral Vectors for Gene Transfer and Expression, Biotechniques, 7:980-2, 984-6, 989-90, 1989). The retroviral vector containing the V3 gene (LV3SN), as well as the empty control vector (LXSN) (FIG. 1), were used to infect cultured aortic SMC from Fischer rats using PA317 packaging cells as previously described (Miller, A. D. and Rosman, G. J., Improved Retroviral Vectors for Gene Transfer and Expression, Biotechniques, 7: 980-2, 984-6, 989-90, 1989; Clowes, M. M., Lynch, C. M., Miller, A. D., Miller, D. G., Osborne, W. R., and Clowes, A. W., Long-Term Biological Response of Injured Rat Carotid Artery Seeded with Smooth Muscle Cells Expressing Retrovirally Introduced Human Genes, J Clin Invest., 93:644-51, 1994; Corsaro, C. M. and Pearson, M. L., Enhancing the Efficiency of DNA-Mediated Gene Transfer in Mammalian Cells, Somatic Cell Genet., 7:603-16, 1981).

Cell Culture: Aortic SMC from male Fischer 344 rats were obtained and cultured as described previously (Clowes, M. M., Lynch, C. M., Miller, A. D., Miller, D. G., Osborne, W. R., and Clowes, A. W., Long-Term Biological Response of Injured Rat Carotid Artery Seeded with Smooth Muscle Cells Expressing Retrovirally Introduced Human Genes, J Clin. Invest., 93:644-51, 1994.). Three separate transfections were carried out on cells of different passages: transfection 1 (T1), passage 15 cells; T2, passage 7 cells; and T3, passage 9 cells. Transfected cells were selected by means of the neomycin analogue G418 (800 mg/ml) and maintained in DME high glucose medium (Irvine Scientific #9024) supplemented with 10% FBS (Atlantic Biologicals cat. #S1150) sodium pyruvate (IS #9334), non-essential amino acids (IS #9304) and glutamine pen-strep (IS #9316). Cells were used for experiments between 5 and 9 passages after initial transfections.

Northern Analysis: RNA was isolated and Northern analysis was performed as previously described (Lemire, J., Braun, K., Maurel, P., Kaplan, E., Schwartz, S., and Wight, T., Versican/PG-M Isoforms in Vascular Smooth Muscle Cells, Arterioscler. Thromb. Vasc. Biol., 19:1630-1639, 1999). The rat V3 sequence, rVe, was excised from the pBSM13+ vector using Xho I and Eco RI and used as a DNA probe. To confirm the direction of insertion of the V3 sequence in rat cells transfected with LV3SN, an identical blot was probed with an antisense probe. Antisense RNA probe was prepared by linearizing the rVe plasmid with Xho I, and transcribing in vitro with T3 RNA polymerase, in the presence of α-[$^{32}$P]UTP, using a kit from Ampliscribe. Blots were hybridized as for DNA probes and washed 3× for 5 min in 2×SSPE/0.1% SDS at room temperature, 2× for 5 min in 0.3 ×SSPE/0.1 % SDS, 2× for 15 min in 0.1×SSPE/0.1% SDS. SDS was washed from the blots and single stranded probe was digested from the blots with 40 ug/ml RNase A in 300 mM NaCl, 10 mM Tris, 5 mM EDTA pH 7.4 for 30 min and washed with 0.1×SSPE/0.1% SDS for 15 min.

Western Analysis: Growth and Migration Studies: Growth studies were carried out in 12 well plates. Cells were plated at a density of 2.5×10$^3$/ well and maintained in 2 ml of medium supplemented with 10% FBS. Duplicate wells were counted by haemocytometer at intervals indicated in the results. For migration studies confluent cultures of LXSN and LV3SN transfected FRSMC in 60 mm dishes were scraped with a 1.5 cm wide soft plastic cell scraper to produce a cell-free zone bordered by a straight wound edge. A fine gauge sterile hypodermic needle was used to mark migration reference points in the cell-free zone and adjacent to the wound edge. Photographs were taken immediately after wounding and at intervals up to 72 hours and migration rates calculated for cells moving from the wound edge into the cell-free space.

Visualization of Pericellular Matrix: Visualization of the pericellular coat was done using a particle-exclusion assay as previously described (Evanko, S. P., Angello, J. C., and Wight, T. N., Formation of Hyaluronan- and Versican-Rich Pericellular Matrix is Required for Proliferation and Migration of Vascular Smooth Muscle Cells, Arterioscler Thromb Vasc Biol., 19:1004-13, 1999). Fixed, washed, human red blood cells suspended in TBS were introduced into sparse cultures of LXSN and LV3SN FRSMC and allowed to settle for 15 minutes before photographing. The red blood cells were sterically excluded from the HA/versican cell coat and produced a clear zone adjacent to cell margins.

Electron Microscopy, Interference Microscopy, and Morphometrics: Confluent cultures (5 days) of LXSN and LV3SN transfected FRSMC were fixed in 2% paraformaldehyde and 2% gluteraldehyde in 0.1 M phosphate buffer pH 7.3, processed, and embedded in 60 mm dishes. Resin blocks, including the embedded cell layers, were cleaved from the plastic substrate and sectioned at right angles to the original plastic substratum. Sections were mounted on coated grids and viewed on an electron microscope.

Transfected LXSN and LV3SN FRSMC for interference microscopy were cultured for 24 hrs on glass coverslips, fixed as for electron microscopy for 20 minutes and washed 3 times in TBS. Coverslips were inverted over TBS-filled wells on glass slides and viewed by an interference microscope (courtesy of AW at the Hope Heart Institute).

The area and distribution of close (~30 nm from undersurface of cell to substratum) and focal (~10 nm separation) contacts was determined by point counting from the interference microscopy micrographs. A transparent point-counting grid (100 points) was overlaid on each micrograph and the area fractions for close, focal, and total (close+focal) contacts, and area fractions for regions of non-contact (>30 nm separation), determined for vector-alone and V3 transfected cells.

Results

Figure 2:
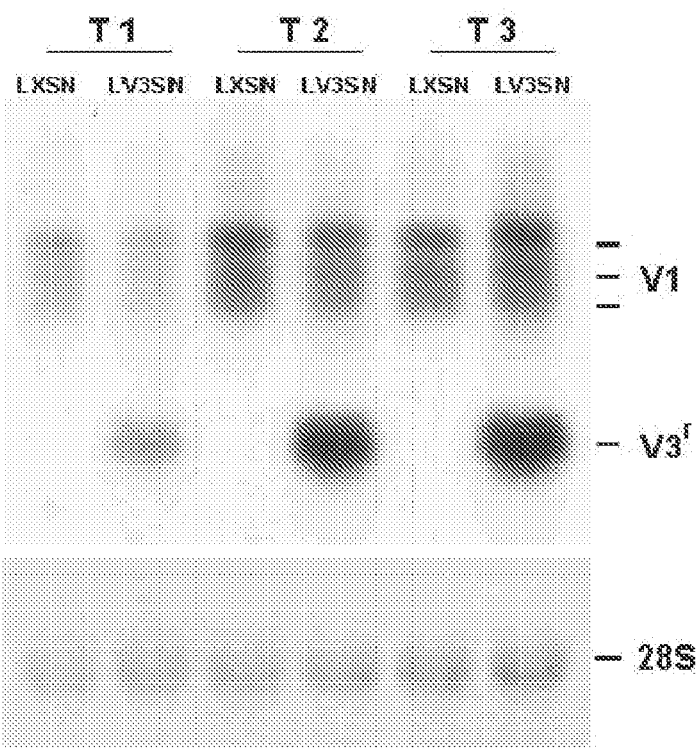
FIG. 2. Northern blot of mRNA from vector-alone (LX) and V3 (LV) transfected FRSMC lines T1, T2 and T3 probed for V3 expression with a versican sequence recognizing both recombinant V3 (V3r) and V1 isoforms. Lower panel shows gel loading intensities for 28S RNA.

V3 Expression: All three FRSMC LV3SN transfected lines (T1, T2, and T3) expressed V3 mRNA, with strong expression in the two lower passage lines T2 and T3 (FIG. 2). All three vector-alone LXSN cell lines, each established from the same cell pools as their corresponding LV3SN transfected line, were negative for V3 expression. As predicted, the V3 probe recognized mRNA for the versican isoform V1 in all vector-alone and LV3SN lines. LV3SN levels were generally similar to control LXSN levels, slightly reduced for lines T1 and T2 and slightly increased for line T3. Generally V1 expression levels matched V3 expression with lower levels of expression in the T1 line and higher levels in the T2 and T3 lines (FIG. 2). The expression of the V3 message in the sense direction as confirmed by hybridization to antisense V3 RNA probe, which also hybridized to the V1 message (data not shown).

Figure 3:
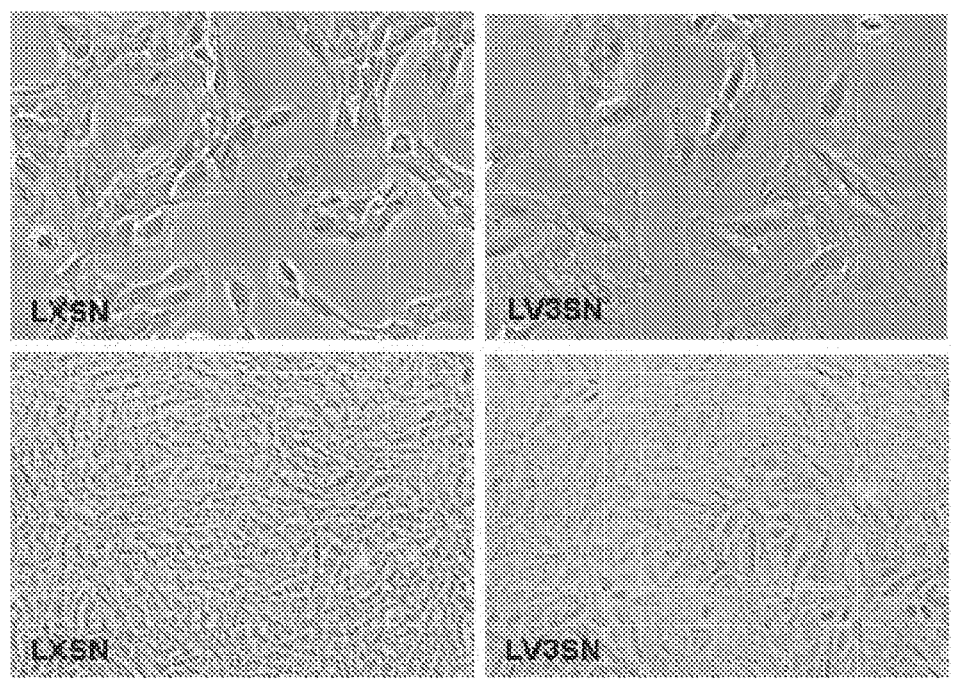
FIG. 3. Morphologies of cultured vector-alone (LXSN) and V3 (LV3SN) transfected FRSMC (line T2) 24 hrs after seeding (upper panels) and at confluence (lower panels). V3 cells are flatter, more spread, and less spindle shaped than vector-alone cells.

Cell morphology in culture: LV3SN transfected FRSMC were more flattened, more spread, and less fusiform in shape than their LXSN controls. These differences were evident soon after seeding and attachment and were clearly visible in low-density 24 hour cultures (FIG. 3). Differences were maintained during extended periods of cell growth and were again clearly discernible in high density multi-layered cultures (FIG. 3).

Figure 4:
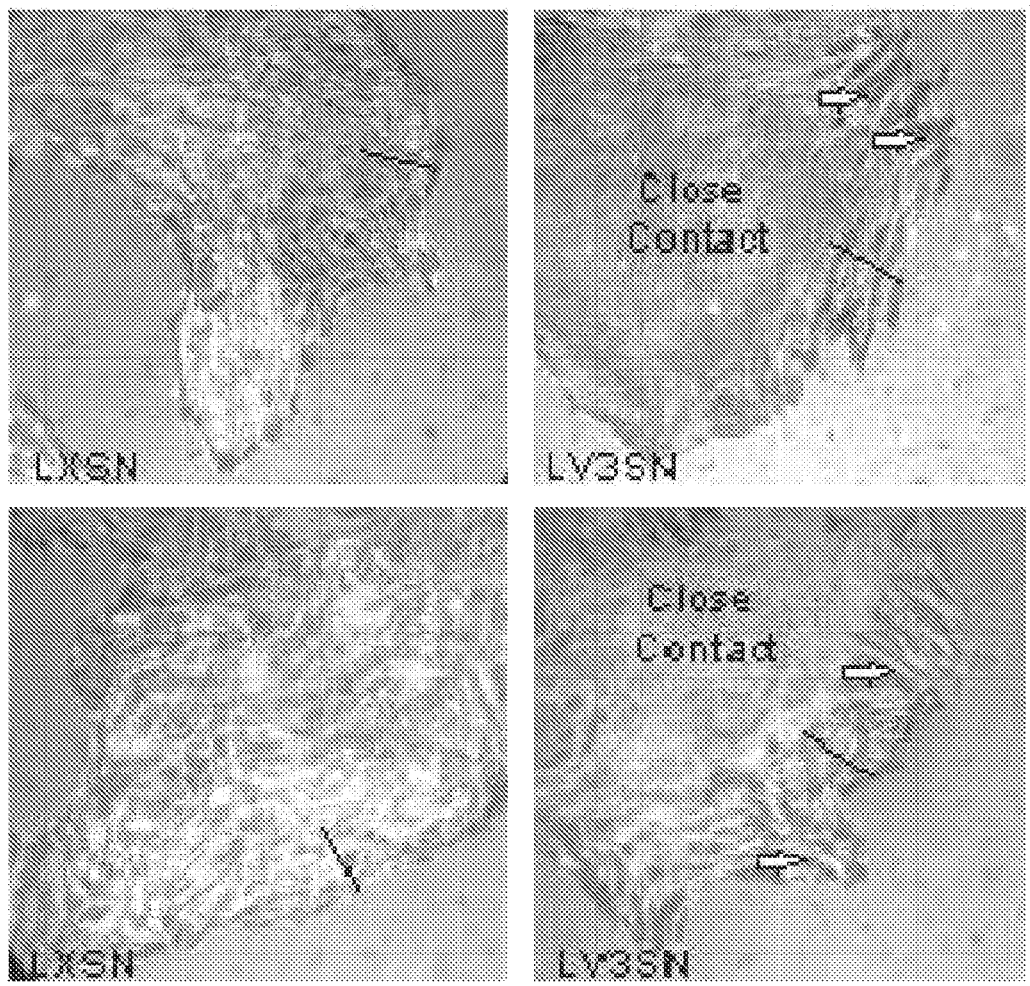
FIG. 4. Interference microscopy images of the undersurface of 24 hr cultured LXSN and LV3SN transfected FRSMC showing close contacts (homogeneous medium gray areas) and focal contacts (small dark elongated areas indicated by arrows). V3 cells are characterized by large areas of close contacts (~30 nm from undersurface of cell to substratum) and by peripheral and radially orientated focal contacts (~10 nm separation). LXSN cells have little or no areas of close contacts and smaller and more widely distributed focal contacts. For explanation of the black bars see legend for FIG. 5.
Figure 5A:
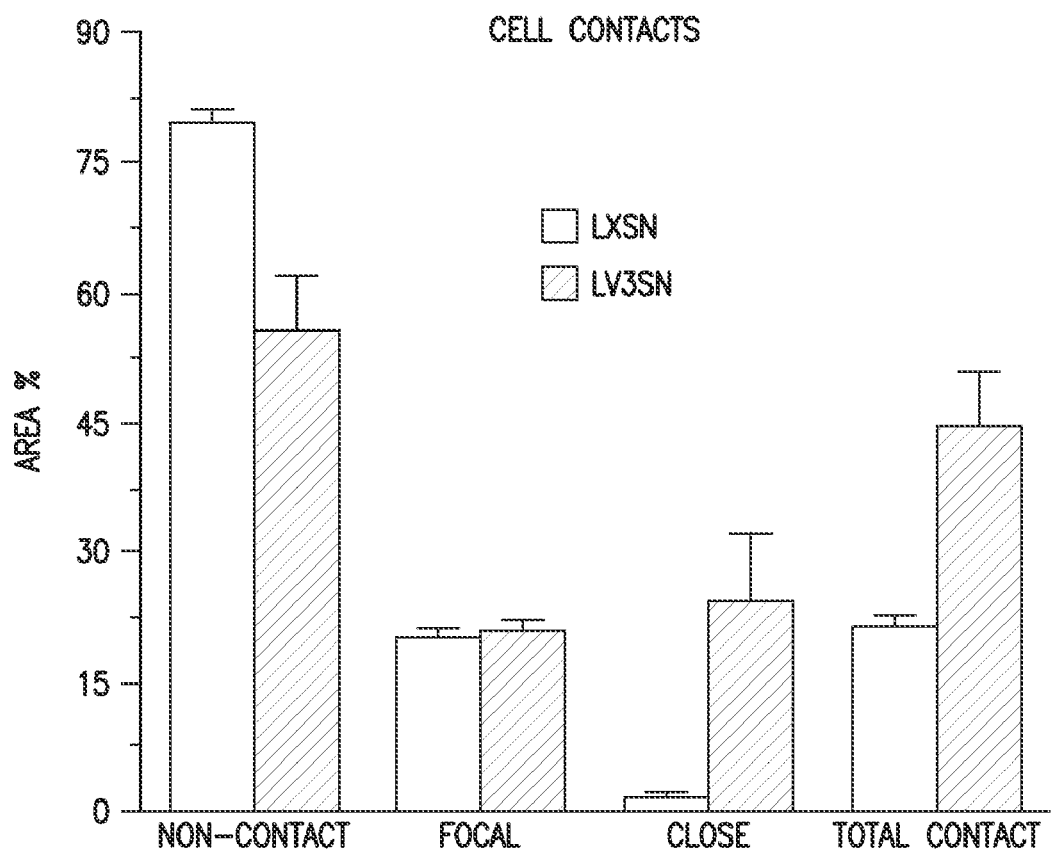
FIG. 5. (a) Area occupied, as a percent of total cell substrate area, by close, focal and total (close+focal) contacts, and by regions of non-contact, in 24 hr cultured LXSN and LV3SN transfected FRSMC (line T2). Data (means ( SE, n=8) are from point counting of interference microscopy images. The area occupied by regions of close contacts was significantly ($p>0.02$) greater in the V3 cells compared with vector-alone cells whereas focal contact area was not significant different (NSD). (b) Comparison of the number and relative sizes of focal contacts around the perimeter of LXSN and LV3SN FRSMC. The width of the zone sampled is indicated by the black bars in FIG. 4. Whereas the number of focal contacts/unit area was not significantly different, the mean size was significantly ($p>0.003$) larger in V3 cells compared with vector-alone cells.
Figure 5B:
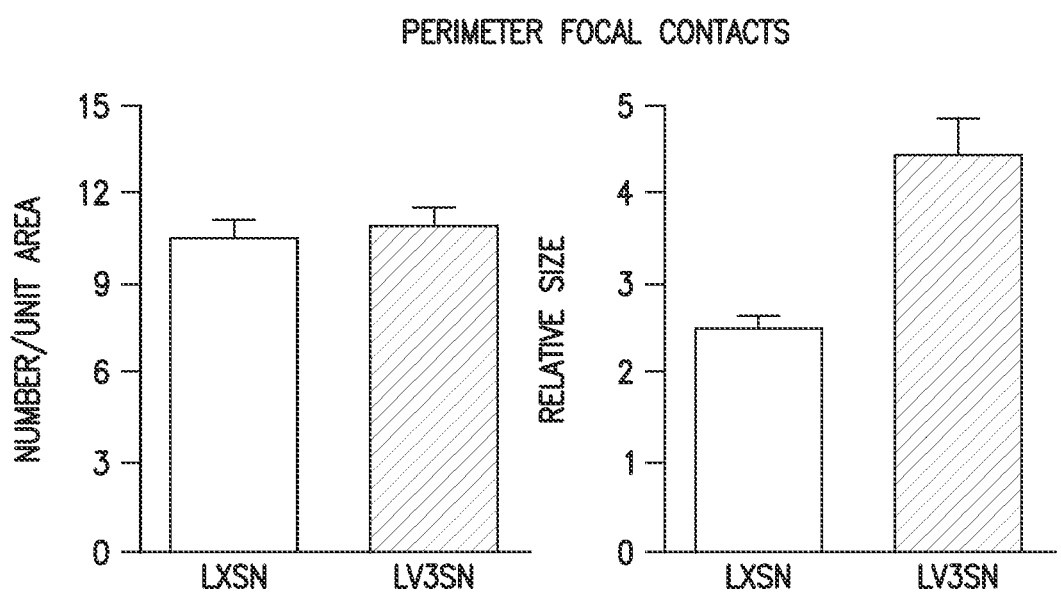

Other V3-associated changes in morphology were seen in interference microscopy images of the undersurface of cells cultured at low density on glass coverslips (FIG. 4). LV3SN FRSMC were characterized by two distinctive features; large areas of close contacts, regions where the undersurfaces of cells were separated from the culture substratum by approximately 30 nm, and prominent, peripherally located and radially orientated, focal contacts, separated from the substratum by approximately 10 nm. In contrast, close contacts in LXSN cells were rare. Focal contacts, while present and similar in number compared with LV3SN cells, were smaller and more widely distributed. These observations on types, distributions and sizes of contacts were confirmed by a morphometric analysis (FIG. 5).

Figure 6A:
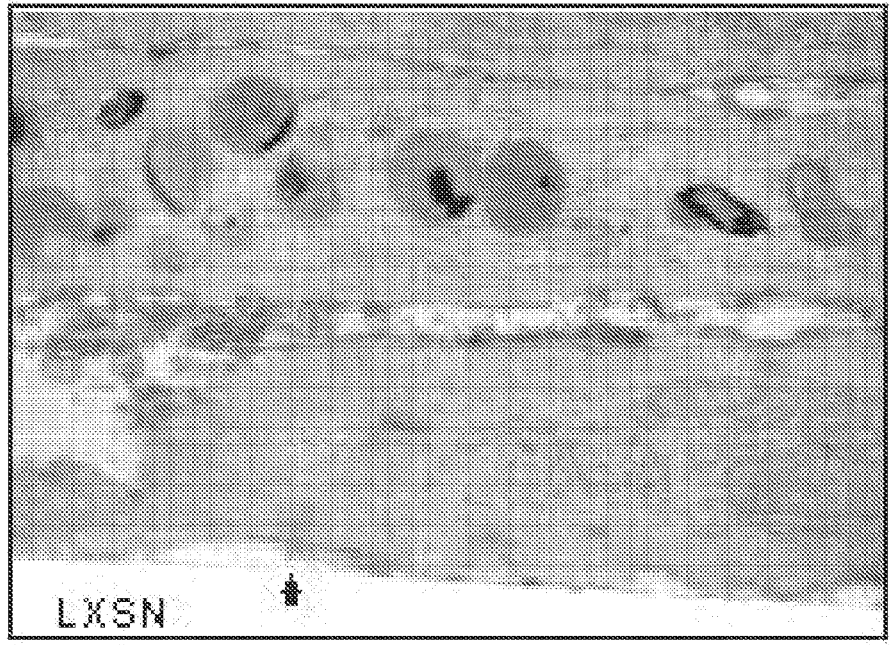
FIG. 6. Electron micrographs of cultured confluent (5 days) and multilayered LXSN and LV3SN transfected FRSMC. Cells are sectioned at right angles to the bottom of the culture dish. The lower straight edge in each micrograph marks the region of contact with the plastic substrate. Note that whereas the vector-alone cells make intermittent contact, V3 cells are closely applied to the substratum.
Figure 6B:
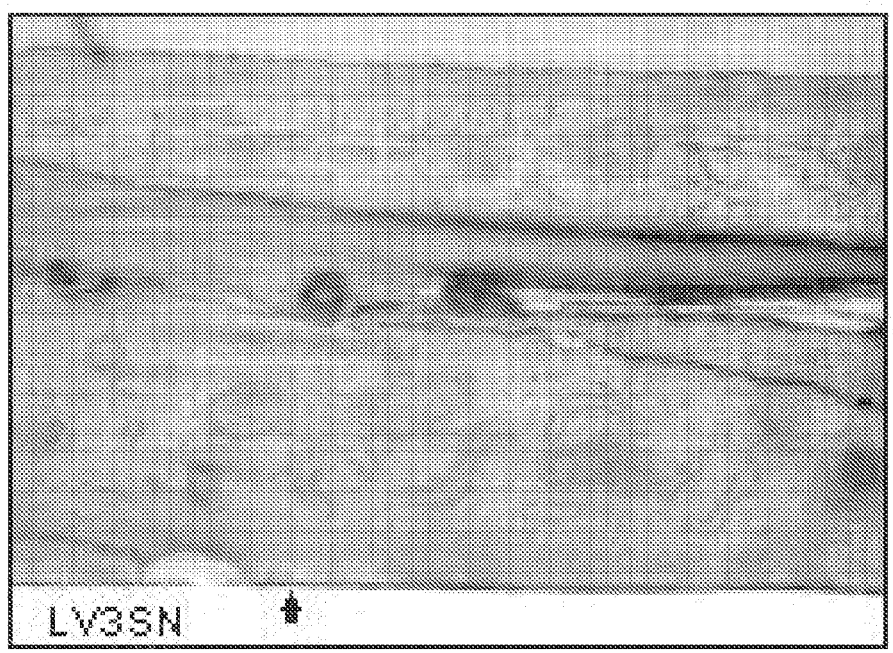

Electron microscopy of confluent cultures also confirmed that LV3SN cells were closely applied to the substratum (FIG. 6). In some regions the layered LV3SN cells were closely applied to each other with little intervening matrix (FIG. 6, lower panel). In other regions, however, matrix separated the cells and the arrangement was indistinguishable from that seen for the vector-alone cells (FIG. 6, upper panel).

Figure 7A:
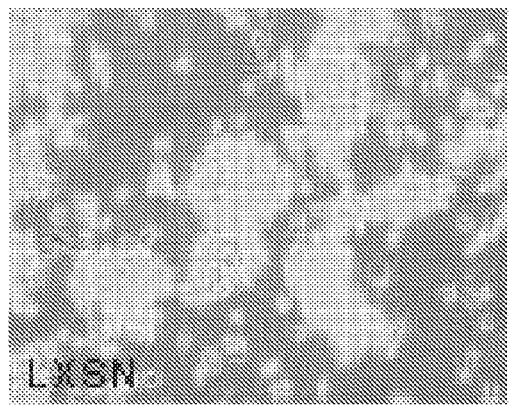
FIG. 7. Sensitivity of confluent cultures of LXSN and LV3SN transfected FRSMC (line T2) to 3 minutes of trypsinization. V3 cells are more resistant to rounding and detachment.
Figure 7B:
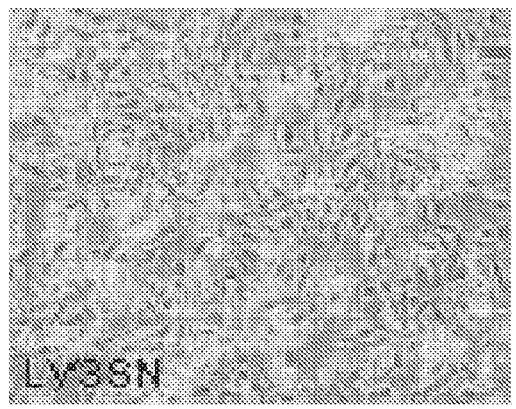
Figure 8A:
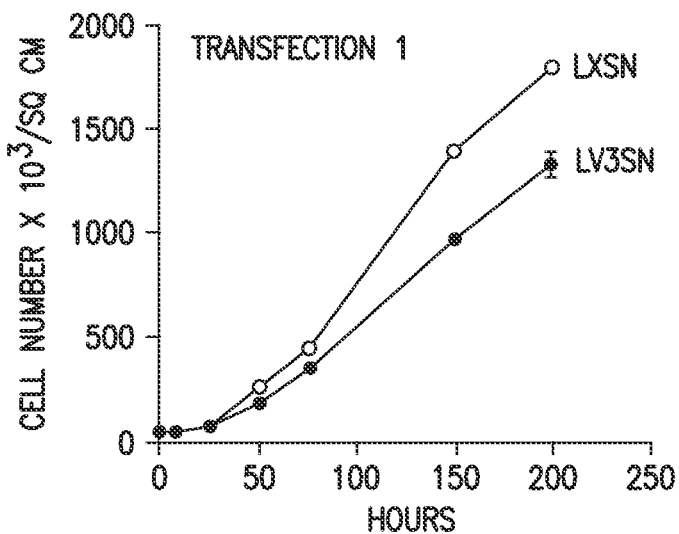
FIG. 8. Proliferation (upper panels) and migration (lower panels) of LXSN and LV3SN transfected FRSMC lines 1, 2, and 3. Migration distances were measured from the original wound edges, created by scraping confluent cultures, to the leading margins of migrating cells. Error bars for proliferation data are the range of duplicates, for migration data SEs for n=5.
Figure 8B:
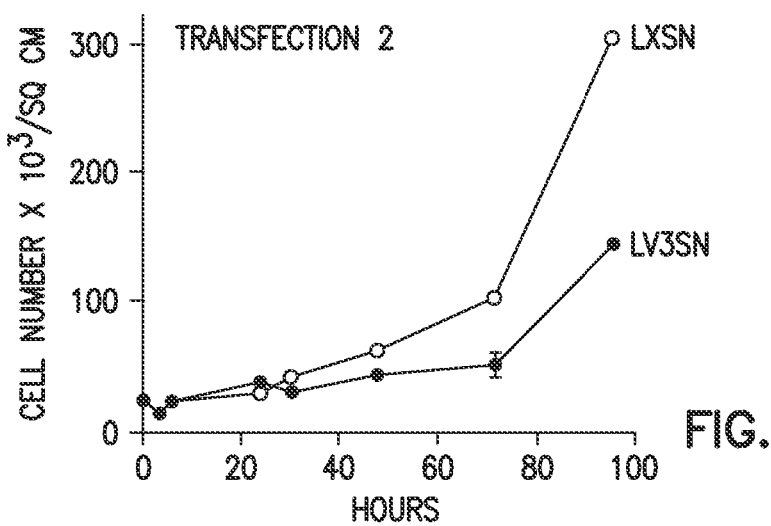
Figure 8C:
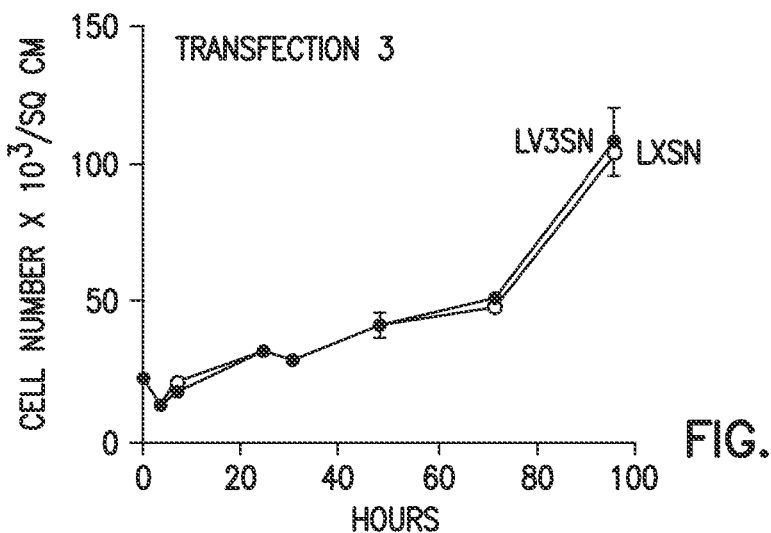
Figure 8D:
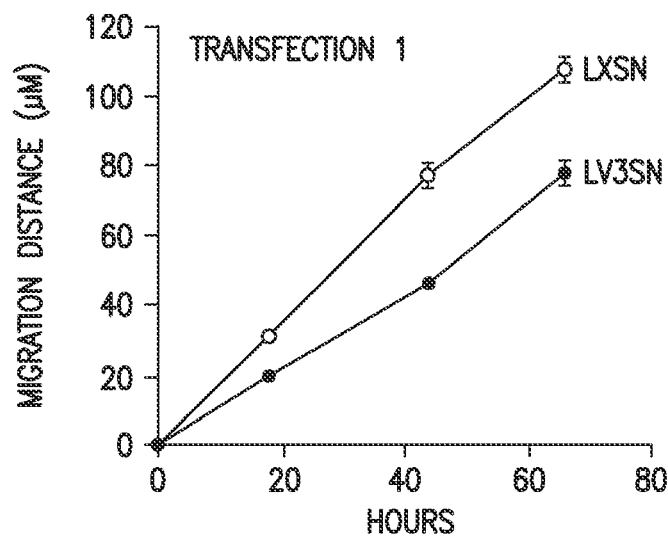
Figure 8E:
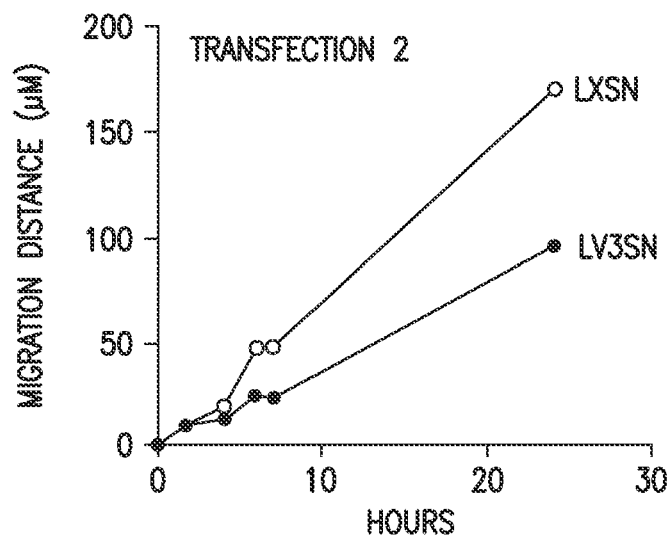
Figure 8F:
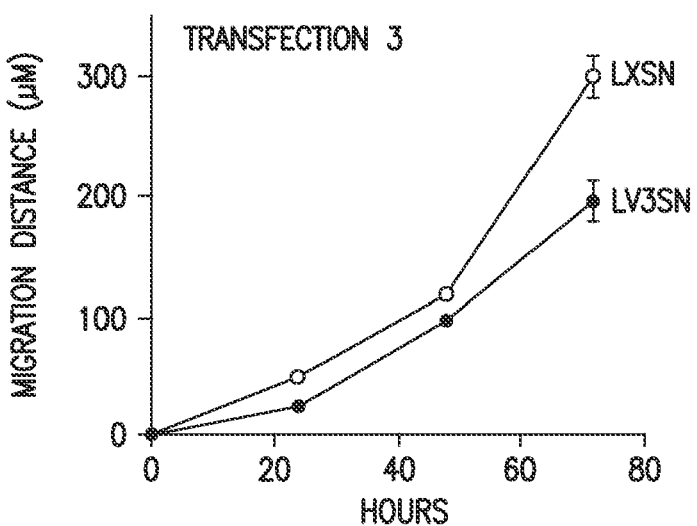

Trypsin/EDTA sensitivity: LV3SN transfected FRSMC were significantly more resistant to trypsin/EDTA detachment than LXSN cells trypsinized for the same length of time (FIG. 7). All three pairs of transfected lines of LV3SN and LXSN (T1, T2, and T3) showed similar differential responses.

Growth and migration: LV3SN cell lines showed slower rates of growth, (with the exception of the T3 line), and slower rates of migration from a wound edge, compared with their LXSN controls (FIG. 8). The slower rate of migration for the LV3SN cells was evident soon after wounding and significantly retarded by 10 hrs. At longer time periods after wounding (48-72 hrs) the migration rates for LV3SN and LXSN were similar but the initial difference generally maintained.

Visualization of Pericellular Coat: Addition of fixed red blood cells (RBC) to low density cultures of LV3SN and LXSN FRSMC confirmed the flattened morphology of LV3SN cells and further demonstrated a reduced cell coat in the V3 transfected cells. In the LV3SN cells the RBC settled directly over the flattened upper surface as well as immediately alongside or over the cell margins. In contrast the RBC rolled to the margins of the raised LXSN cells and in most cells settled several microns away from the cell margins, indicating the presence of a pericellular coat (FIG. 9).

Discussion

Applicants have expressed in vitro a natural splice variant, V3, which differs from the larger versican variants in at least two ways: it is much shorter and lacks CS chains. These differences may have functional consequences. V3, however, is composed of the G1 and G3 sequences which are present in the other versican isoforms (Zako, M., Shinomura, T., Ujita, M., Ito, K., and Kimata, K., Expression of PG-M(V3), an Alternatively Spliced Form of PG-M without a Chondroitin Sulfate Attachment Region in Mouse and Human Tissues, J. Biol. Chem., 270:3914-3918, 1995), so that it also seems likely that V3 would share many of the functions of the larger variants.

Applicants have discovered that cells overexpressing V3 are more adhesive than control cells. This finding may seem surprising, in that versican has long been considered an anti-adhesive molecule (Yamagata, M., Suzuki, S., Akiyama, S. K., Yamada, K. M., Kimata, K., Regulation of Cell-Substrate Adhesion by Proteoglycans Immbolized on Extracellular Substrates, J. Biol. Chem., 264:9012-8018, 1989). These anti-adhesive properties are dependent on the attachment of the chondroitin sulfate chains to the protein cores (Yamagata, M., Suzuki, S., Akiyama, S. K., Yamada, K. M., Kimata, K., Regulation of Cell-Substrate Adhesion by Proteoglycans Immbolized on Extracellular Substrates, J. Biol. Chem., 264: 9012-8018, 1989), thus we might have predicted that V3, lacking CS chains, would have no affect on adhesion. Rather than having no effect on cell adhesion, however, we have found that the overexpression of V3 increases the size of focal contacts, increases the ratio of close contact to non-contact regions, and makes cells more resistant to removal from the substratum with trypsin.

Much of the anti-adhesive effect of the larger versican isoforms is probably due to their binding to HA (LeBaron, R. G., Zimmermann, D. R., and Ruoslahti, E., Hyaluronate Binding Properties of Versican, J. Biol. Chem., 267:10003-10010, 1992) to form large pericellular coats which exclude red blood cells in vitro (Evanko, S. P., Angello, J. C., and Wight, T. N., Formation of Hyaluronan- and Versican-Rich Pericellular Matrix is Required for Proliferation and Migration of Vascular Smooth Muscle Cells, Arterioscler Thromb Vasc Biol., 19:1004-13, 1999). In vivo these coats may prevent the interaction of the cell with other matrix molecules or with other cells. Indeed, versican, HA, and CD44, a receptor for HA, are excluded from focal contacts (Ang, L. C., Zhang, Y., Cao, L., Yang, B. L., Young, B., Kiani, C., Lee, V., Allan, K., and Yang, B. B., Versican Enhances Locomotion of Astrocytoma Cells and Reduces Cell Adhesion through its G1 Domain, J Neuropathol Exp Neurol., 58:597-605, 1999). We hypothesize that V3, which contains the HA-binding G1 domain, may increase adhesion by competing with and replacing larger, anti-adhesive, versican isoforms in pericellular coats. Our findings are consistent with this hypothesis. However, if this is the mechanism by which V3 increases adhesion in smooth muscle cells, we would have expected that expression of the HA-binding globular domain (G1) alone would also increase adhesion. Experiments, however, show that the G1 domain of versican, like an internally truncated versican which has 15% of the CS-attachment domain, is anti-adhesive when transfected into NIH 3T3 cells and when added to astrocytoma cell cultures (Yang, B. L., Zhang, Y., Cao, L. Yang, B. B., Cell Adhesion and Proliferation Mediated Through the G1 Domain of Versican, J. Cell Biochem., 72:210-220, 1999; Zimmermann, D. R., Dours Zimmermann, M. T., Schubert, M., and Bruckner Tuderman, L., Versican is Expressed in the Proliferating Zone in the Epidermis and in Association with the Elastic Network of the Dermis, J. Cell Biol., 124:817-825, 1994).

If V3 does not displace the proteoglycan forms of versican, it may exert its effects by altering the total versican concentration. Studies with chondrocytes and aggrecan, a molecule related to versican, show that the effects of aggrecan are concentration-dependent and dependent on the presence of another homologous molecule, link protein, which is essentially an independent G1 domain. Both aggrecan and link protein, molecules which form a stable ternary complex with HA, independently decrease cell adhesion. When added together, on the other hand, adhesion returned to near normal (Yang, B. B., Zhang, Y., Cao, L., Yang, B. L., Aggrecan and Link Protein Affect Cell Adhesion to Culture Plates and to Type II Collagen, Matrix Biol., 16:541-561, 1998). Versican, link protein and HA are believed to form similar stable complexes (Binette, F., Cravens, J., Kahoussi, B., Haudenschild, D., and Goetinck, P., Link Protein is Ubiquitously Expressed in Non-Cartilaginous Tissues where it Enhances and Stabilizes the Interaction of Proteoglycans with Hyaluronic Acid, J. Biol. Chem., 269:19116-19122, 1994). Overexpression of V3 may change the versican/link protein ratio, thereby altering the stability of these ternary complexes and thus affect adhesion. The different responses of fibroblasts to the G6 domain versus ASMC to V3 (comprising both G1 and G3 domains) (this study and references) may be due to the use of cell types expressing different base-line levels of versican or link protein.

The inhibition of migration by V3 and the reduced proliferation in two of three V3 transfectants may be secondary to the effects of V3 on cell adhesion. Cells must reduce attachment to the substratum for both of these processes to occur. We have previously found that pericellular coats containing HA and versican surround migrating ASMC and displacement of these coats with HA oligosaccharides inhibit both PDGF-stimulated proliferation and migration (Evanko, S. P., Angello, J. C., and Wight, T. N., Formation of Hyaluronan- and Versican-Rich Pericellular Matrix is Required for Proliferation and Migration of Vascular Smooth Muscle Cells, Arterioscler Thromb Vasc Biol., 19:1004-13, 1999). The overexpression of V3 may disrupt these coats by a different mechanism (displacing versican proteoglycan forms or destabilizing the versican:link:HA complex) leading to similar effects on proliferation and migration. Versican containing a shortened CS domain has also been shown to promote migration of astrocytoma cells in a scratch wound assay (Ang, L. C., Zhang, Y., Cao, L., Yang, B. L., Young, B., Kiani, C., Lee, V., Allan, K., and Yang, B. B., Versican Enhances Locomotion of Astrocytoma Cells and Reduces Cell Adhesion through its G1 Domain, J Neuropathol Exp Neurol., 58:597-605, 1999) and to stimulate proliferation (Zhang, Y., Cao, L., Yang, B. L., and Yang, B. B., The G3 Domain of Versican Enhances Cell Proliferation via Epidermal Growth Factor-like Motifs, J Biol. Chem., 273:21342-51, 1998; Hinek, A., Boyle, J., and Rabinovitch, M., Vascular Smooth Muscle Cell Detachment from Elastin and Migration through Elastic Laminae is Promoted by Chondroitin Sulfate-induced "shedding" of the 67-kDa Cell Surface Elastin Binding Protein, Exp. Cell Res., 203:344-353, 1992). It was not determined whether the CS chains in this mini-versican construct contribute to the cell migration, but chondroitin sulfate, even when not attached to protein cores, has been shown to promote migration of ASMC by causing the shedding of an elastin/laminin binding protein (Hinek, A., Boyle, J., and Rabinovitch, M., Vascular Smooth Muscle Cell Detachment from Elastin and Migration through Elastic Laminae is Promoted by Chondroitin Sulfate-induced "shedding" of the 67-kDa Cell Surface Elastin Binding Protein, Exp. Cell Res., 203:344-353, 1992). The G1 domain was shown to stimulate both proliferation and migration, whereas the G3 domain stimulates proliferation via its EGF-like domains and does not promote migration. Because V3 is composed of the G1 and G3 domains, we hypothesized that the function of V3 might be the sum of the functions of the individual domains. Our findings that V3 inhibited migration and reduced proliferation suggests, however, that V3 is more than a sum of its parts.

Although V3 may modulate cell behavior by altering pericellular coats, it may also effect behavior by more conventional means, i.e. by binding to cell surface receptors or to another matrix protein. The recombinant G1 domain of the homologous protein aggrecan binds better to the cell surface of hyaluronidase-treated chondrocytes (Cao, L., Zhang, Y., and Yang, B., Expression of the G1 Domain of Aggrecan Interferes with Chondrocyte Attachment and Adhesion, Matrix Biol., 17:379-392, 1998), suggesting that a cell surface receptor for that domain may exist. The G3 domain consists of multiple conserved elements (EGF-like, lectin-like and complement-regulatory protein-like (CRP-like)) which may interact with other molecules. It is not clear why V3, which contains the EGF-like motifs which are apparently active in the mini-versican construct and in the isolated G3 domain (Zhang, Y., Cao, L., Yang, B. L., and Yang, B. B., The G3 Domain of Versican Enhances Cell Proliferation via Epidermal Growth Factor-like Motifs, J Biol Chem., 273:21342-51, 1998), inhibits proliferation. It is possible that, in the V3 isoform, the proximity of the EGF-like domain to the HA binding region (Zako, M., Shinomura, T., Ujita, M., Ito, K., and Kimata, K., Expression of PG-M(V3), an Alternatively Spliced Form of PG-M without a Chondroitin Sulfate Attachment Region in Mouse and Human Tissues, J. Biol. Chem., 270:3914-3918, 1995) instead of to the extended GAG-attachment region, alters the secondary structure of the EGF-like domains sufficiently to prevent interactions with the EGF receptor. It is also possible that the unique sequence formed by the junction between the G1 and G3 domains has a function that is unique to the V3 variant.

V3 may effect cell function more indirectly for example by changing the organization of other matrix molecules. The G3 domain has known matrix ligands: tenascin-R and fibulin-1 (Aspberg, A., Binkert, C., and Ruoslahti, E., The Versican C-type Lectin Domain Recognizes the Adhesion Protein Tenascin-R, Proc. Natl. Acad. Sci. USA., 92:10590-10594, 1995; Aspberg, A., Adam, S., Kostka, G., Timpl, R., and Heinegard, D. Fibulin-1 is a Ligand for the C-type Lectin Domains of Aggrecan and Versican, J. Biol. Chem., 274:20444-20449, 1999) are ligands for the lectin-like region. For example, versican is associated with elastic fibrils (Zimmermann, D. R., Dours Zimmermann, M. T., Schubert, M., and Bruckner Tuderman, L., Versican is Expressed in the Proliferating Zone in the Epidermis and in Association with the Elastic Network of the Dermis, J. Cell Biol., 124:817-825, 1994), and its lectin-like region has been shown to bind to fibulin-1, a component of these fibers (Aspberg, A., Adam, S., Kostka, G., Timpl, R., and Heinegard, D., Fibulin-1 is a Ligand for the C-type Lectin Domains of Aggrecan and Versican, J. Biol. Chem., 274:20444-20449, 1999; Miosge, N., Sasaki, T., Chu, M., Herken, R., and Timpl, R., Ultrastructural Localization of Microfibrillar Fibulin-1 and Fibulin-2 During Heart Development Indicates a Switch in Molecular Associations, Cell. Mol. Life Sci., 54:606-613, 1998). If either V3 or large versican CSPG interacts with the elastic fibers during fibrogenesis they may alter the matrix environment. Large versican forms may exclude other proteins, much as the pericellular coat excludes red blood cells. Indeed, addition of exogenous CS to cultures has been shown to displace elastin binding protein from the cell surface and to result in the formation of small fibrils (Hinek, A., Mecham, R., Keeley, F., and Rabinovitch, M., Impaired Elastin Fiber Assembly Related to Reduced 67-kD Elastin-Binding Protein in Fetal Lamb Ductus Arteriosus and in Cultured Aortic Smooth Muscle Cells Treated with Chondroitin Sulfate, J. Clin. Invest., 88:2083-2094, 1991). Instead of producing an impenetrable coat, small versican forms might instead bring other versican ligands in proximity to the forming fibers.

Although the in vivo function of the V3 molecule is unclear, our results suggest that it can counteract the function of the large versican CSPG variants. Versican CSPG is a normal component of many tissues (Bode-Lesniewska, B., Dours-Zimmermann, M., Odermatt, B., Briner, J., Heitz, P., and Zimmerman, D., Distribution of the Large Aggregating Proteoglycan Versican in Adult Human Tissue, J. Histochem. Cytochem., 44:303-312, 1996; Wight, T. N., Lara, S., Riessen, R., LeBaron, R., Isner, J., Selective Deposits of Versican in the Extracellular Matrix from Human Peripheral Arteries, Am. J. Pathol., 151:963-973, 1997), but its elevation in a number of disease processes may be detrimental to health. The space filling property of versican CSPG may contribute to vascular restenosis (Bode-Lesniewska, B., Dours-Zimmermann, M:, Odermatt, B., Briner, J., Heitz, P., and Zimmerman, D., Distribution of the Large Aggregating Proteoglycan Versican in Adult Human Tissue, J. Histochem. Cytochem., 44:303-312, 1996) and the CS chains bind lipoproteins (Srinivasan, S. R., Xu, J. H., Vijayagopal, P., Radhakrishnamurthy, B., and Berenson, G. S., Low-Density Lipoprotein Binding Affinity of Arterial Chondroitn Sulfate Proteoglycan Variants Modulates Cholesteryl Ester Accumulation in Macrophages, Biochem. Biophys Acta., 1272:61-67, 1995) and thus contribute to vascular lipid deposition during atherogenesis. Further, versican is elevated in tumor stroma (Isogai, Z., Shinomura, T., Yamakawa, N., Takeuchi, J., Tsuji, T., Heinegard, D., and Kimata, K., 2B1 Antigen Characteristically Expressed on Extracellular Matrices of Human Malignant Tumors is a Large Chondroitin Sulfate Proteoglycan, PG-M/versican, Cancer Res., 56:3902-3908; Nara, Y., Kato, Y., Torii, Y., Tsuji, Y., Nakagaki, S., Goto, S., Isobe, H., Nakashima, N., and Takeuchi, J., Immunohistochemical Localization of Extracellular Matrix Components in Human Breast Tumors with Special Reference to PG-M/versican, Histochem. J., 29:21-30, 1997) and increases astrocytoma cell migration in vitro (Zimmermann, D. R., Dours Zimmermann, M. T., Schubert, M., and Bruckner Tuderman, L. Versican is Expressed in the Proliferating Zone in the Epidermis and in Association with the Elastic Network of the Dermis, J. Cell Biol., 124:817-825, 1994). An understanding of the mechanisms that control the differential splicing of the versican RNA, or specific targeting of the CSPG isoforms for destruction, may have health benefits.

EXAMPLE 2

Methods and Materials

Retroviral transfection: Transfection of Fischer rat aortic SMC with V3 has been described previously (Lemire, J. M., Braun, K. R., Maurel, P., Kaplan, E. D., Schwartz, S. M., Wight, T. N., Versican/PG-M Isoforms in Vascular Smooth Muscle Cells, Arterioscler. Thromb. Vasc. Biol., 19:1630-1639, 1999). Briefly, rat V3 cDNA, rVe(Lemire, 1999, #448), had an upstream sequence of 18T's which we believed to be an artifact of its cloning into the vector in the reverse direction. To remove this sequence, the V3 sequence was prepared as follows, using standard molecular biology protocols. The rVe cDNA in pBSM13+ was linearized with Nar 1, at position −188 of the 5' untranslated region. The overhanging ends were filled-in with Klenow fragment and Bam HI linkers were attached. After digestion with Bam HI, which cut both the linker and a sequence in the multicloning site at the other end of the versican sequence, the V3 sequence was inserted into the Bam HI site of the retroviral vector LXSN (courtesy of Dr. A. D. Miller, Fred Hutchinson Cancer Research Center, Seattle, Wash.). The retroviral vector containing the V3 gene (LV3SN), as well as the empty control vector (LXSN) (FIG. 1), were used to infect cultured aortic SMC from Fischer rats using PA317 packaging cells as previously described.

Cell Culture: Aortic SMC from male Fischer 344 rats were obtained and cultured as described previously (Fischer, J. W., Kinsella, M. G., Clowes, M. M., Lara, S., Clowes, A. W., Wight, T. N., Local Expression of Bovine Decorin by Cell-Mediated Gene Transfer Reduces Neointimal Formation After Balloon Injury in Rats, Circ. Res., 86:676-683, 2000). Three separate transfections were carried out on cells of different passages: transfection 1 (T1), passage 15 cells; T2, passage 7 cells; and T3, passage 9 cells. Transfected cells were selected by means of the neomycin analogue G418 (800 µg/ml) and maintained in DME high glucose medium (Irvine Scientific #9024) supplemented with 10% FBS (Atlantic Biologicals cat. #S11150) sodium pyruvate (IS #9334), non-essential amino acids (IS #9304) and glutamine pen-strep (IS #9316). Cells were used for experiments between 5 and 9 passages after initial transfections.

Northern Analysis of V3 and Tropoelastin: RNA was isolated and Northern analysis was performed as previously described. The rat V3 sequence, rVe, was excised from the pBSM 13+ vector using Xho I and Eco RI and used as a DNA probe. To confirm the direction of insertion of the V3 sequence in rat cells transfected with LV3SN, an identical blot was probed with an antisense probe. Antisense RNA probe was prepared by linearizing the rVe plasmid with Xho I, and transcribing in vitro with T3 RNA polymerase, in the presence of $\alpha$-[$^{32}$P]UTP, using a kit from Ampliscribe. Blots were hybridized as for DNA probes (tropoelastin probe). Blots were hybridized, washed 3× for 5 min each in 2×SSPE/ 0.1% SDS at room temperature, 2× for 15 min each in 0.3× SSPE/0. 1% SDS, 2× for 15 min each in 0.1×SSPE/0.1% SDS. SDS was washed from the blots and single stranded probe was digested from the blots with 40 ug/ml RNase A in 300 mM NaCl, 10 mM Tris, 5 mM EDTA, pH 7.4 for 30 min and washed with 0.1×SSPE/0.1% SDS for 15 min.

Conditioned Medium Experiments: Tropoelastin mRNA levels were determined for vector-alone LXSN SMC cultures maintained for 24 hrs in media conditioned for approximately 48 hours on LV3SN cultures and mixed with LXSN conditioned media. Dilution ratios ranged from 5:1 to 0:1 LXSN/ LV3SN. Changes in mRNA levels were normalized to 28S loading intensities.

Balloon Injury and Cell Seeding: Balloon injury and cell seeding in Fisher 344 rats were performed as described previously. The distal half of the left common carotid artery was surgically exposed and isolated and a 2F balloon catheter introduced through an arteriotomy in the external branch. The balloon was passaged 3 times through the left common carotid artery in order to remove the endothelium. The transfected SMCs were trypsinized and approximately 1×10$^5$ of either LXSN or LV3SN SMCs in 0.04 ml of culture medium infused into the isolated carotid segment. Three animals received LXSN cells and six animals the LV3SN cells. The seeded SMCs were allowed to adhere for 15 minutes. Subsequently the catheter was removed, the external carotid ligated, blood flow restored, and the wound closed. Animals were maintained on a normal diet for 4 weeks and the animals sacrificed with an overdose of pentibarbital. All surgical procedures were performed according to the Principles of Laboratory Animal Care and the Guild for the Care and Use of Laboratory Animals (National Institutes of Health publication No. 86-23, revised 1985).

Proliferative Index of Intimal SMC: LXSN and LV3SN rats received 50 mg bromdeoxyruidine (BrdU) subcutaneously 24 hours before sacrifice. Subsequently, sections from paraffin-embedded carotids were stained for BrdU with a specific monoclonal antibody to BrdU (Boehringer Mannheim, Indianapolis, Ind.). BrdU-positive and -negative nuclei were counted under a microscope and proliferative indices (% BrdU-positive cells) determined for intimas formed from LXSN and LV3SN cells.

Histo- and Immunocytochemistry: Sections from paraffin-embedded carotids were stained with H&E, Massons Trichrome, and orcein to show general morphology, collagen, and elastin respectively.

Electron Microscopy and Morphometrics: Confluent 3 week old cultures of LXSN and LV3SN transfected FRSMC were fixed in 2% paraformaldehyde and 2.5% glutaraldehyde in 0.1 M phosphate buffer pH 7.3, processed, and embedded in 60 mm dishes. Resin blocks, which included the embedded cell layers, were cleaved from the plastic substrate and sectioned at right angles to the original plastic substratum.

Following the overdose of pentobarbital animals for histo- and immunocyto-chemistry were fixed by perfusion with 10% neutral buffered formalin at 120 mmHg of pressure for 5 minutes. Subsequently ballooned injured and seeded vessels and the non-injured contralateral controls were excised, processed for embedding, and sectioned. Segments of carotid artery for electron microscopy were fixed in 3% glutaraldehyde in 0.1 M cacodylate buffer, secondarily fixed in 1% OsO$_4$, processed, and sectioned at right angles to the vessel axis. Thin sections of cells, mounted on formvar coated grids, and vessels were stained and viewed on a microscope.

Volume fractions for cell and matrix components of the cultured material and the carotids were determined by point counting. A transparent point-counting grid (100 points) was overlaid on each micrograph and mean volume fractions calculated for individual components.

Statistics: Data were analyzed by Students T Test and a probability of 0.05 taken as significant.

Results

V3 expression: As previously shown (Lemire, J. M., Braun, K. R., Maurel, P., Kaplan, E. D., Schwartz, S. M., Wight, T. N., Versican/PG-M Isoforms in Vascular Smooth Cells, Arterioscler. Thromb. Vasc. Biol., 19:1630-1639, 1999) all three FRSMC V3 transfected lines (T1, T2, and T3) expressed V3 mRNA with strong expression in the two lower passage lines T2 and T3 (see FIG. 13, upper panel). All three vector-alone LXSN lines, established from the same cell pools as their corresponding LV3SN transfected line, were negative for V3 expression. The expression of the V3 message in the sense direction was confirmed by hybridization to antisense V3 RNA probe, which also hybridized to the V1 message (data not shown).

Morphology of long-term cultures: Dense multi-layered long-term (3 week) cultures of LXSN and LV3SN FRSMC retained their respective distinctive morphological features seen in short-term cultures and reported previously (Leimre et al., submitted). Compared with vector-alone cells, V3 cells were more spread, flatter, and less spindle shaped (FIG. 10). The most notable difference, however, and one not seen in short-term cultures, was the presence of an irregular network of fibers, especially prominent around the periphery of cells adherent to the culture dish.

Figure 11A:
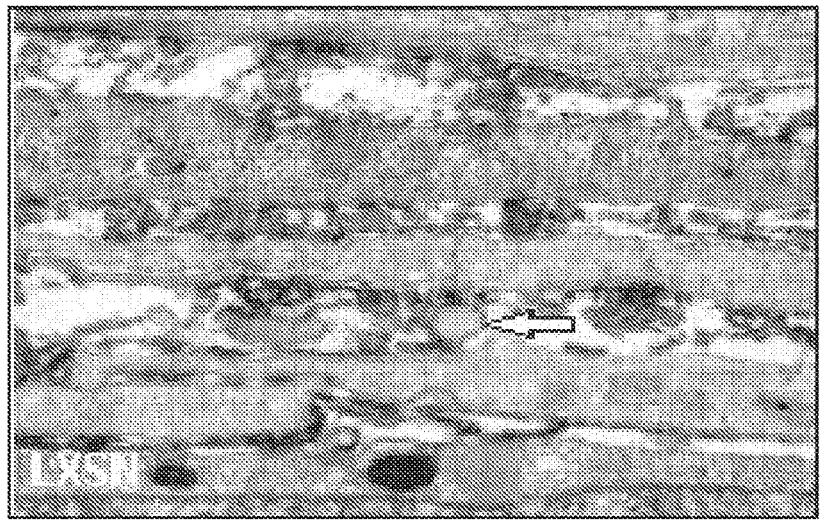
FIG. 11. Electron micrographs of multi-layered 3-week cultures of LXSN (upper panel) and LV3SN FRSMC (middle and lower panels), sectioned perpendicular to the substratum, showing more prominent elastin deposits (arrows) in V3 compared with vector-alone cultures. Insert shows typical large elastin deposit between cells and substratum in V3 culture. Lower panel shows close association of elastin and cell surface (arrows).
Figure 11B:
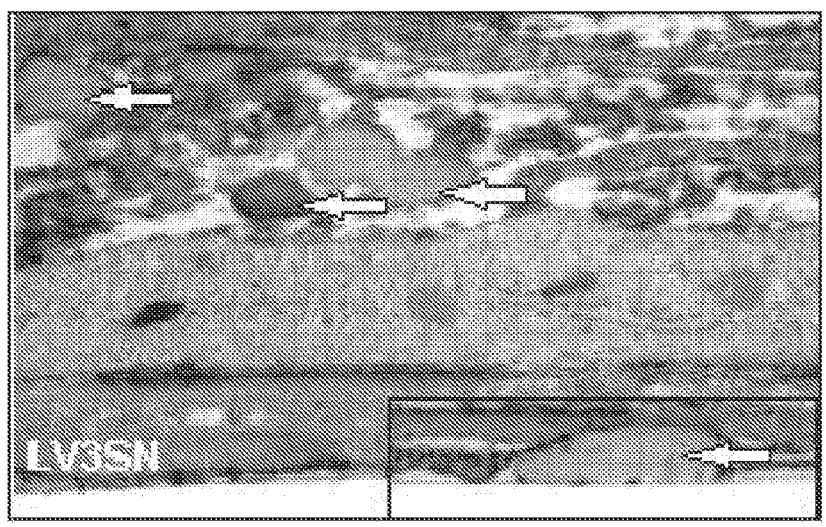
Figure 11C:
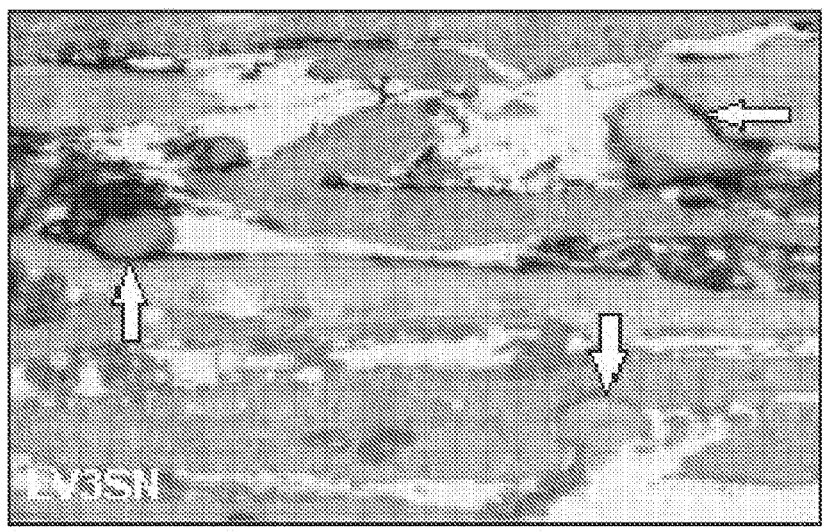

Electron microscopy of these cultures showed that the network was made of elastic fibers (FIG. 11, middle panel) deposited extracellularly between the layered cells and with especially prominent deposits between the substratum and the adjacent cells. It was notable that many of the elastin deposits were closely associated with cell surfaces (FIG. 11 lower panel). The vector-alone cultures also contained elastic fibers but these were fewer in number and smaller (FIG. 11 upper panel).

Figure 12A:
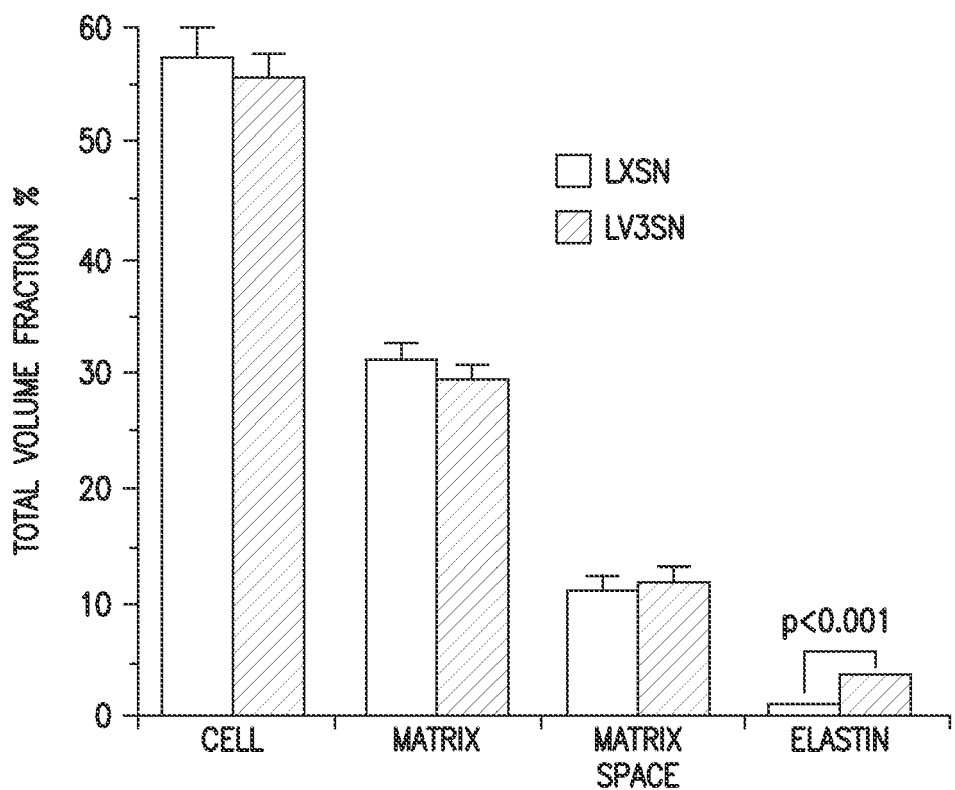
FIG. 12. (a) Volume fractions, determined from electron micrographs, for cells, matrix (including collagen), matrix space (areas devoid of staining), and elastin in 3-week cultures of LXSN and V3 FRSMC. Values are means and standard errors for transfections 2 and 3 combined. (b) LXSN and LV3SN volume fractions of elastin for transfections 2 (T2) and 3 (T3) graphed separately and combined. The numbers above the standard errors are the numbers of electron micrographs analyzed by point counting. Note the higher volume fraction for T3 LXSN compared with T2 LXSN cells (see FIG. 5).
Figure 12B:
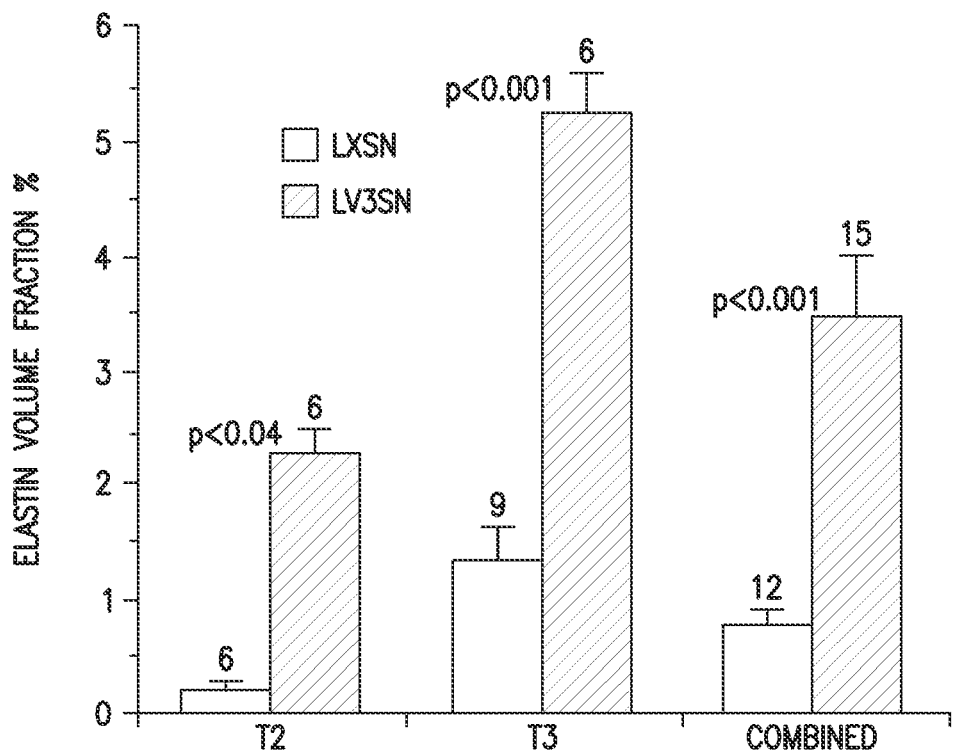

This was confirmed by morphometric analysis (FIG. 12). Volume fractions, determined by point counting, for cells, matrix, matrix space, and elastin, showed that the primary difference in components between the vector-alone and the V3 cultures was the fraction occupied by elastin. Analysis of the T2 and the T3 lines separately (FIG. 12b) showed that the V3 cells of both lines had a significantly higher volume fraction than their corresponding vector-alone control. It was also noted that the vector-alone T3 cell line had a higher volume fraction of elastin than the T2 line (see below).

Figure 13:
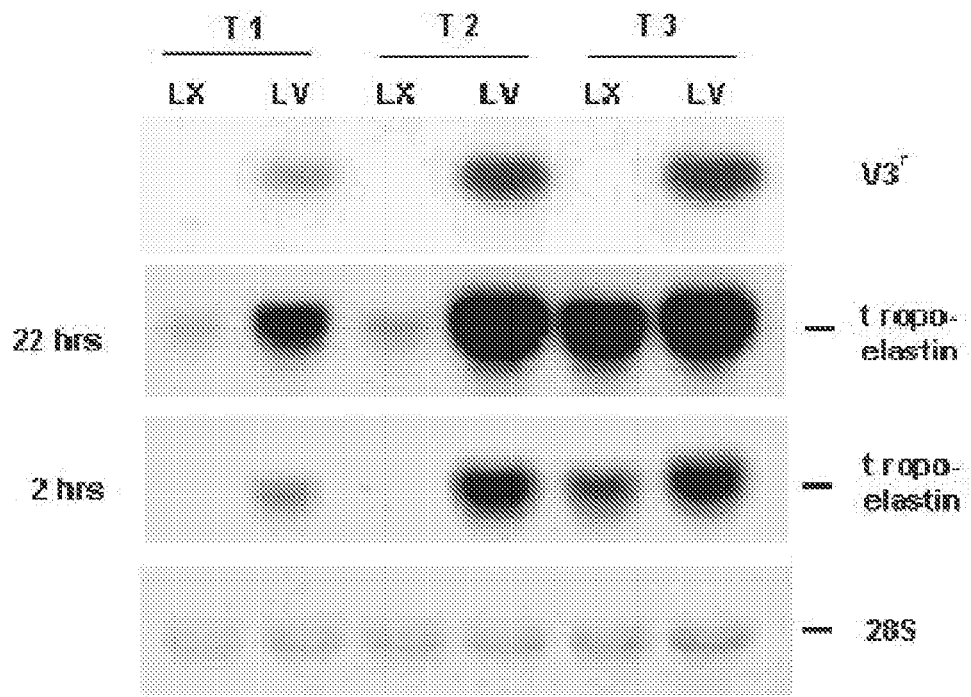
FIG. 13. Northern blots of mRNA from vector-alone (LX) and V3 (LV) transfected FRSMC lines T1, T2, and T3 probed for V3 expression, with a versican sequence recognizing the recombinant V3 (V3r), and for rat tropoelastin. The 24 hr exposure period shows clear up-regulation of tropelastin in V3 cells of the T1 and T2 compared with their respective LX controls. The 2 hr exposure period shows the increased expression of tropelastin in V3 cells compared with LX control which had a higher level of expression than the T 1 and T2 control lines, a feature consistent with the higher volume fraction of elastin in T3 LX cultures (see FIG. 12). Lower panel shows loading densities.
Figure 14:
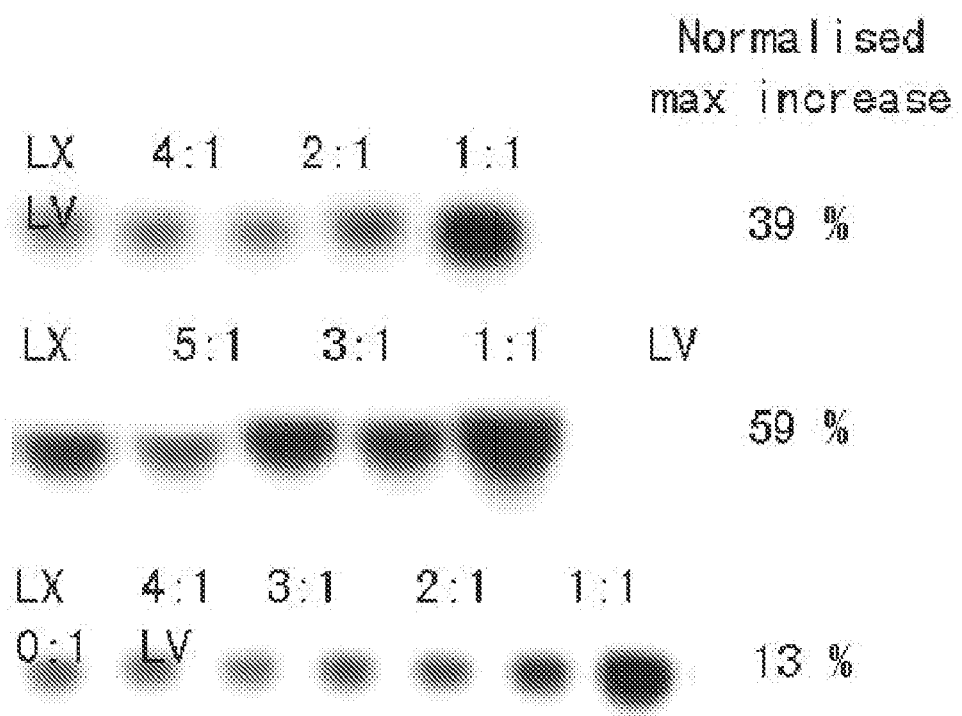
FIG. 14. Northern blots of mRNA from vector-alone transfected cells (LX), vector-alone cells exposed to increasing proportions (left to right) of conditioned medium from V3 cells mixed with medium from LX cells, and V3 transfected cells (LV), probed with rat tropoelastin. The percentage maximum increases were normalized against 28S densities.

Tropoelastin mRNA levels: Northern blots of mRNA from cultures of LXSN and LV3SN cultured and probed with rat tropoelastin showed marked upregulation in the V3 cells (FIG. 13). Importantly these levels were determined for mRNA isolated from confluent week-old cultures and before the elastin fiber network was visible by light microscopy. It was further noted that tropoelastin mRNA levels in the vector-alone transfected lines T2 and T3 differed and matched elastic fiber volume fractions in the long term cultures (FIG. 12). The T3 control cells had a significantly higher level of tropoelastin mRNA than the T2 cells and had a correspondingly higher volume fraction of elastin.

Conditioned media transfer: Media conditioned on confluent LV3SN cultures, mixed with varying proportions of conditioned media from LXSN cultures, and transferred to LXSN cultures, caused a small but consistent increase in tropelastin expression ranging from 13 to 59% normalized to 28S loading intensities. These increases, however, were generally only apparent for media containing a high proportion of V3 conditioned medium.

Figure 15:
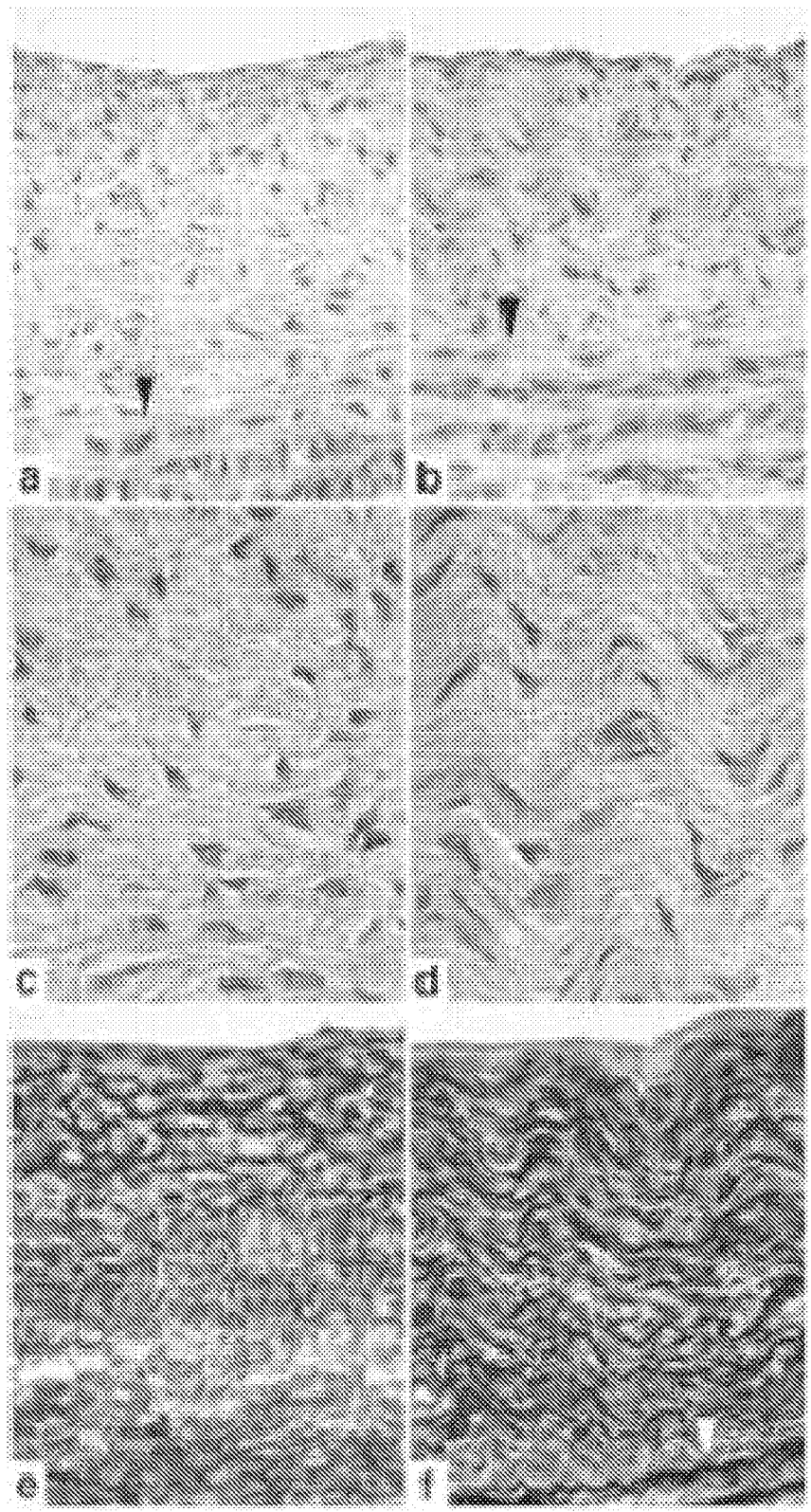
FIG. 15. Light micrographs of neointima formed from vector-alone (a, c, e) and V3 (b, d, f) transfected FRSMC seeded into ballooned rat carotid arteries and stained with Masson trichrome (collagen blue/green) (a, b, c, d) and orcein (elastin dark blue) (e, f). Arrow heads indicate intimal/medial interface.

Neointima formed from V3 cells seeded into ballooned rat carotid arteries differed significantly from neointima formed by vector-alone cells (FIG. 15). Control neointima was characterized by typical stellate or rounded SMC (FIGS. 15a and 15c) embedded in a myxoid matrix containing mostly randomly oriented bundles of collagen (15c) and elastic (15e) fibers. In contrast, V3 neointima was highly structured with elongated and circumferentially arranged SMC (FIGS. 7b and d) embedded in a compact matrix of collagen (15d) and elastin (15f), the latter arranged in lamellar-like layers more similar to a developing media than a typical neointima.

Figure 16:
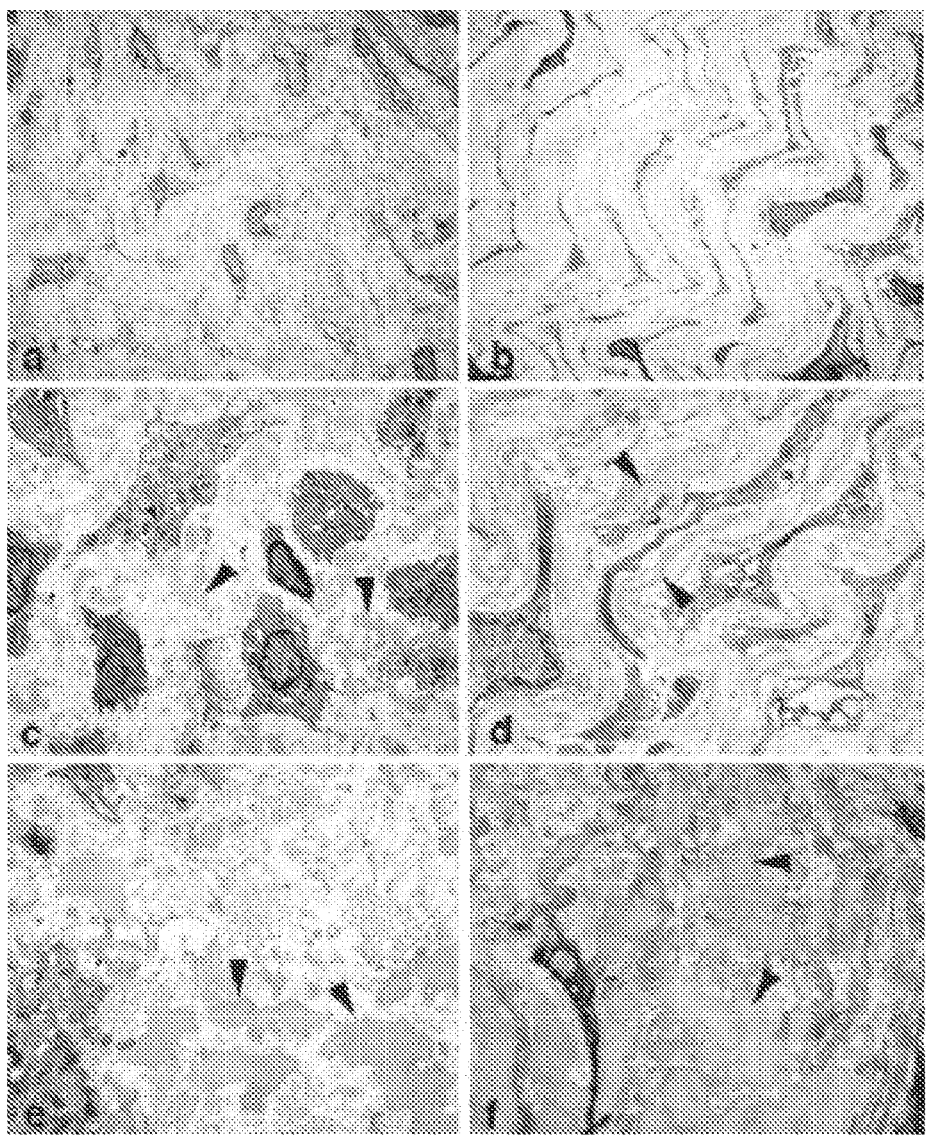
FIG. 16. Electron micrographs of neointima formed from vector-alone (a, c, e) and V3 (b, d, f) transfected FRSMC seeded into ballooned rat carotid arteries. Vector-alone transfected SMC form a typical neointima of generally rounded cells and an unstructured matrix of collagen, proteoglycans and elastin (arrow heads). In contrast V3 SMC are elongated and sandwiched between layers of dense extracellular matrix with prominent deposits of elastin (arrow heads), often organized into lamellae (b).
Figure 17:
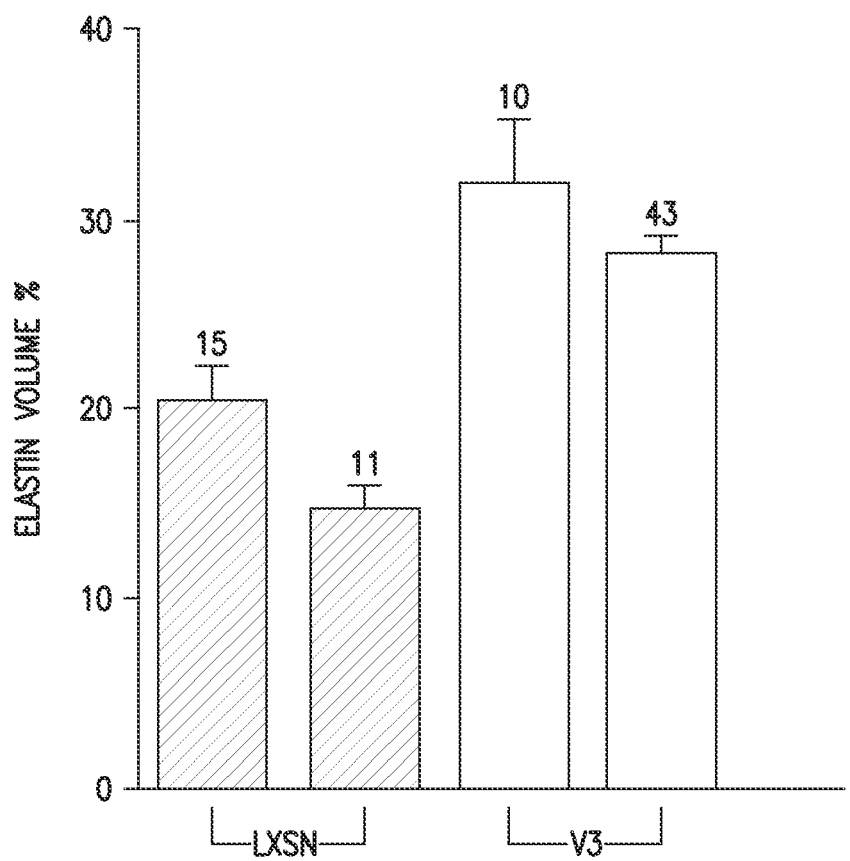
FIG. 17. Volume fractions, determined from electron micrographs, for neointimal elastin deposited by vector-alone (LXSN) and V3 transfected FRSMC. The columns are for individual animals and the number above each standard error bar is the number of micrographs analyzed by point counting.

Electron microscopy further demonstrated differences between neointimas formed from V3 and vector-alone cells (FIG. 16). Compared with the control SMC (FIGS. 16a and 16c), V3 SMC (FIGS. 16b and 16d) were greatly attenuated and aligned in parallel arrays between a dense matrix of collagen and elastin. The elastin was often arranged in bilaminar sheets between adjacent SMC (FIG. 16d). In some regions the elastin was less organized and was arranged as bundles of fibers (FIG. 16f) similar to that seen for vector-alone neointima (FIG. 16e). The total volume fraction of elastin, determined by point counting from electron micrographs, was significantly higher in neointima formed by V3 transfected cells (FIG. 17).

SUMMARY

Thus, V3 transfected rat SMCs show marked up-regulation of tropoelastin synthesis with the formation of networks of elastic fibers in long term cultures. Further, V3 SMC seeded into ballooned rat carotid arteries express V3 and produce a highly structured compact, media-like neointima enriched in elastin deposited as fibres and lamellae.

The invention has been described with reference to various specific and preferred embodiments and techniques. However, it should be understood that many variations and modifications may be made while remaining within the spirit and scope of the invention. Additionally, all publications, patents, and patent documents are incorporated by reference herein, as though individually incorporated by reference. The following list of documents are also incorporated by reference herein, as though individually incorporated by reference: Wight, T., The Role of Matrix in In-Stent Restensois and Restenosis After Balloon Angioplasty, Abstract, Sixth International Drug Delivery Meeting, Geneva, Switzerland, Jan., 27, 2000; Merrilees, M., Lemire, J., Fischer, J., Braun, K., and Wight T., Alteration of Smooth Muscle Cell Phenotype Through Retroviral Insertion of the Gene for Versican Variant V3, Abstract, Fourth Pan Pacific Connective Tissue Societies Symposium, Queenstown, New Zealand, November, 1999 (In: Proceedings of the MBSANZ Vol. 13); U.S. Pat. No. 5,180,808; WO 91/08230; WO 00/68361; Schmalfeldt, M., Bandtlow, C. E., Dours-Zimmerman, M. T., Winterhalter, K. H., Zimmerman, D .R., Brain Derived Versican V2 is a Potent Inhibitor of Axomal, J. Cell Sci., 113:807-816, 2000; Lemire, J. M., Braun, K. R., Maurel, P., Kaplan, E. D., Schwartz, S. M., Wight, T. N., Versican/PG-M Isoforms in Vascular Smooth Muscle Cells, Arteriosclerosis, Thrombosis & Vascular Biology, 19:1630-1639, 1999; Niederost, B. P., Zimmermann, D. R., Schwab, M. E., Bandtlow, C. E., Bovince CNS Myelin Contains Neurite Growth-Inhibitory Activity Associated with Chondroitin Sulfate Proteoglycans, J. of Neuroscience, 19:8979-8989, 1999; Schmalfeldt, M., Dours-Zimmermann, M. T., Winterhalter, K. H., Zimmerman, D. R., Versican V2 is a Major Extracellular matrix Component of the Mature Bovine Brain, J. of Biological Chem., 273:15758-15764, 1998; Milev, P., Maurel, P., Chiba, A., Mevissen, M., Popp, S., Yamaguchi, Y., Margolis, R. K., Margolis, R. U., Differential Regulation of Expression of Hyaluronan-Binding Proteoglycans in Developing Brain: Aggrecan, Versican, Neurocan and Brevican, Biochem. & Biophys. Res. Comm., 247:207-212, 1998; Paulas, W., Baur, I., Dours-Zimmerman, M. T., Zimmerman, D. R., Differential Expression of Versican Isoforms in Brain, J. of Neuropathology & Experimental Neurology, 55:528-533, 1996; Landolt, R. M., Vaughan, L., Winterhalter, K. H., Zimmermann, D. R., Versican is Selectively Expressed in Embryonic Tissues that Act as Barriers to Neural Crest Cell Migration and Axon Outgrowth, Development, 121:2303-2312, 1995; Naso, M. F., Zimmermann, D. R., Iozzo, R. V., Characterization of the Complete Genomic Structure of the Human Versican Gene and Functional Analysis of its Promoter, J. Biological Chem., 269:32999-3008, 1994; Dours-Zimmermann, M. T., Zimmerman, D. R., A Novel Glycosaminoglycan Attachment Domain Identified in Two Alternative Splice Variants of Human Versican, J. Biological Chem., 269:32992-32998, 1994; and Cleary, E. G., Gibson, M. A., "Elastic Tissue, Elastin and Elastin Associated Microfibril", In: Extracellular Matrix, Vol. 2, Molecular Components and Interactions, Wayne D. Comper, ed., Harwood Academic Publishers GmbH, the Netherlands, pp. 95-140 (1996).

What is claimed is:

1. A method to inhibit or treat a pathological condition comprising a decrease in elastic fiber formation in a mammal comprising administering to the mammal an effective amount of an expression vector which increases the activity or amount of versican V3, wherein the vector comprises a nucleic acid molecule encoding a versican V3 having SEQ ID NO:2.

2. The method of claim 1, wherein the nucleic acid molecule has SEQ ID NO:1.

3. The method of claim 1, wherein the mammal is a human.

4. The method of claim 1, wherein the vector is administered topically.

5. The method of claim 1, wherein the administration enhances tropoelastin synthesis or increases the amount of elastic fiber in the mammal.

6. The method of claim 1 or 2, wherein the vector is contacted with cells or tissue of the mammal.

7. The method of claim 1, wherein the vector is contacted with a blood vessel of the mammal so as to cause an increase in amount of elastic fiber in the mammalian blood vessel.

8. The method of claim 1 or 2, wherein the vector is contacted with a blood vessel of the mammal.

9. The method of claim 1, wherein the administration increases adhesion of cells of the mammal.

10. The method of claim 1, wherein the administration decreases proliferation of the cells of the mammal.

11. The method of claim 1, wherein the pathological condition is emphysema, Marfan's syndrome or aortic dissections, supravalvular aortic stenosis, Williams syndrome, or congenital contractual arachnodactyly.

12. The method of claim 1 or 2, wherein the administration increases the elastic fiber in mammalian cartilage, promotes wound healing, promotes the growth of elastic fibers in mammalian cartilage, reduces or eliminates wrinkles, or prevents lesion formation following angioplasty.

13. A method to enhance tropoelastin synthesis or formation of elastic fibers in a mammal comprising administering to the mammal an effective amount of an expression vector comprising a nucleic acid molecule encoding a versican V3 having SEQ ID NO:2.

14. The method of claim 1, wherein the condition is lymphangioleiomyomatosis.

15. The method of claim 1, wherein the condition is an aneurysm.

16. The method of claim 1 or 13, wherein the administration alters skin elasticity.

17. The method of claim 1, 3 or 13, wherein mammalian cells or tissue comprising the vector are administered.

18. The method of claim 17, wherein the nucleic acid molecule has SEQ NO:1.

19. The method of claim 17, wherein the cells or tissue are human cells or human tissue.

20. The method of claim 19, wherein the cells or tissue increase the elastic fiber in said mammal.

21. The method of claim 19, wherein said cells or tissue are smooth muscle cells or tissue.

22. The method of claim 19, wherein the cells or tissue are skin or cartilage cells or tissue.

23. The method of claim 19, wherein the cells or tissue are blood vessel cells or tissue.

24. The method of claim 17, wherein growth of the mammalian cells on a scaffold is improved or the seeding capacity of the mammalian cells in a tissue graft is improved.

25. The method of claim 17, wherein tropoelastin synthesis or the amount of elastic fiber in said cells or tissue is enhanced.

26. A method to enhance tropoelastin synthesis in or formation of networks of elastic fibers in a mammalian cells or tissue comprising contacting the mammalian cells or tissue with an effective amount of an expression vector selected to increase said synthesis or formation, said vector comprising a nucleic acid encoding versican V3 having SEQ ID NO:2.

27. The method of claim 26, wherein the contacted cells or tissue are administered to an animal.

28. The method of claim 27, wherein the cells, tissue and mammal are human.

29. The method of claim 26, 27 or 28, wherein the effective amount increases or promotes the growth of the elastic fiber in mammalian cartilage, improves the growth of mammalian cells or tissue on a scaffold, improves the seeding capacity of mammalian cells in a tissue graft, increases the adhesion of cells in the tissue, alters skin elasticity, promotes wound healing, reduces or eliminates wrinkles, or prevents lesion formation following angioplasty.

30. The method of claims 26, wherein the cells or tissue are skin, cartilage, or blood vessel cells or tissue.

31. The method of claim 27 wherein the tissue or cells are skin, cartilage or blood vessel tissue or cells.

32. The method of claim 30 wherein the tissue or cells are grown on a scaffold or in a tissue graft.

* * * * *

SEQUENCE LISTING

<160> NUMBER OF SEQ ID NOS: 2

<210> SEQ ID NO 1
<211> LENGTH: 2087
<212> TYPE: DNA
<213> ORGANISM: Homo sapiens

<400> SEQUENCE: 1

```
caccacgctt cctatgtgac ccgcctgggc aacgccgaac ccagtcgcgc agcgctgcag     60
tgaattttcc ccccaaactg caataagccg ccttccaagg ccaagatgtt cataaatata    120
aagagcatct tatggatgtg ttcaaccttta atagtaaccc atgcgctaca taaagtcaaa    180
gtgggaaaaa gcccaccggt gaggggctcc ctctctggaa aagtcagcct accttgtcat    240
ttttcaacga tgcctacttt gccacccagt tacaacacca gtgaatttct ccgcatcaaa    300
tggtctaaga ttgaagtgga caaaaatgga aaagatttga aagagactac tgtccttgtg    360
gcccaaaatg gaaatatcaa gattggtcag gactacaaag ggagagtgtc tgtgcccaca    420
catcccgagg ctgtgggcga tgcctccctc actgtggtca agctgctggc aagtgatgcg    480
ggtctttacc gctgtgacgt catgtacggg attgaagaca cacaagacac ggtgtcactg    540
actgtggatg gggttgtgtt tcactacagg gcggcaacca gcaggtacac actgaatttt    600
gaggctgctc agaaggcttg tttggacgtt ggggcagtca tagcaactcc agagcagctc    660
tttgctgcct atgaagatgg atttgagcag tgtgacgcag gctggctggc tgatcagact    720
gtcagatatc ccatccgggc tcccagagta ggctgttatg agataagat gggaaaggca    780
ggagtcagga cttatggatt ccgttctccc aggaaaactt acgatgtgta ttgttatgtg    840
gatcatctgg atggtgatgt gttccacctc actgtcccca gtaaattcac cttcgaggag    900
gctgcaaaag agtgtgaaaa ccaggctgcc aggctggcaa cagtggggga actccaggcg    960
gcatggagga acggctttga ccagtgcgat tacgggtggc tgtcggatgc cagcgtgcgc   1020
caccctgtga ctgtggccag ggcccagtgt ggaggtggtc tacttggggt gagaaccctg   1080
tatcgttttg agaaccagac aggcttccct ccccctgata gcagatttga tgcctactgc   1140
tttaaacgac ctgatcgctg caaaatgaac ccgtgcctta acggaggcac ctgttatcct   1200
actgaaactt cctacgtatg cacctgtgtg ccaggataca gcggagacca gtgtgaactt   1260
gattttgatg aatgtcactc taatccctgt cgtaatggag ccacttgtgt tgatggtttt   1320
aacacattca ggtgcctctg ccttccaagt tatgttggtg cactttgtga gcaagatacc   1380
gagacatgtg actatggctg gcacaaattc aagggcagt gctacaaata ctttgcccat   1440
cgacgcacat gggatgcagc tgaacgggaa tgccgtctgc agggtgccca tctcacaagc   1500
atcctgtctc acgaagaaca aatgtttgtt aatcgtgtgg gccatgatta tcagtggata   1560
ggcctcaata caagatgtt tgagcatgac ttccgttgga ctgatggcag cacactgcaa   1620
tacgagaatt ggagacccaa ccagccagac agcttctttt ctgctggaga agactgtgtt   1680
gtaatcattt ggcatgagaa tggccagtgg aatgatgttc cctgcaatta ccatctcacc   1740
tatacgtgca agaaaggaac agttgcttgc ggccagcccc tgttgtaga aaatgccaag   1800
acctttggaa agatgaaacc tcgttatgaa atcaactccc tgattagata ccactgcaaa   1860
gatggtttca ttcaacgtca ccttccaact atccggtgct taggaaatgg aagatgggct   1920
atacctaaaa ttcctgcat gaacccatct gcataccaaa ggacttattc tatgaaatac   1980
tttaaaaatt cctcatcagc aaaggacaat tcaataaata catccaaaca tgatcatcgt   2040
```
tggagccgga ggtggcagga gtcgaggcgc tgatccctaa aatggcg    2087

<210> SEQ ID NO 2
<211> LENGTH: 655
<212> TYPE: PRT
<213> ORGANISM: Homo sapiens

<400> SEQUENCE: 2

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Lys Glu Cys Glu Asn
            260                 265                 270

Gln Ala Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Arg Pro Asp Arg Cys
            340                 345                 350

Lys Met Asn Pro Cys Leu Asn Gly Gly Thr Cys Tyr Pro Thr Glu Thr
        355                 360                 365

-continued

```
Ser Tyr Val Cys Thr Cys Val Pro Gly Tyr Ser Gly Asp Gln Cys Glu
        370             375             380
Leu Asp Phe Asp Glu Cys His Ser Asn Pro Cys Arg Asn Gly Ala Thr
385                 390             395                 400
Cys Val Asp Gly Phe Asn Thr Phe Arg Cys Leu Cys Leu Pro Ser Tyr
                405             410              415
Val Gly Ala Leu Cys Glu Gln Asp Thr Glu Thr Cys Asp Tyr Gly Trp
            420             425             430
His Lys Phe Gln Gly Gln Cys Tyr Lys Tyr Phe Ala His Arg Arg Thr
            435             440             445
Trp Asp Ala Ala Glu Arg Glu Cys Arg Leu Gln Gly Ala His Leu Thr
    450             455             460
Ser Ile Leu Ser His Glu Glu Gln Met Phe Val Asn Arg Val Gly His
465             470             475             480
Asp Tyr Gln Trp Ile Gly Leu Asn Asp Lys Met Phe Glu His Asp Phe
            485             490             495
Arg Trp Thr Asp Gly Ser Thr Leu Gln Tyr Glu Asn Trp Arg Pro Asn
            500             505             510
Gln Pro Asp Ser Phe Phe Ser Ala Gly Glu Asp Cys Val Val Ile Ile
        515             520             525
Trp His Glu Asn Gly Gln Trp Asn Asp Val Pro Cys Asn Tyr His Leu
        530             535             540
Thr Tyr Thr Cys Lys Lys Gly Thr Val Ala Cys Gly Gln Pro Pro Val
545             550             555             560
Val Glu Asn Ala Lys Thr Phe Gly Lys Met Lys Pro Arg Tyr Glu Ile
                565             570             575
Asn Ser Leu Ile Arg Tyr His Cys Lys Asp Gly Phe Ile Gln Arg His
            580             585             590
Leu Pro Thr Ile Arg Cys Leu Gly Asn Gly Arg Trp Ala Ile Pro Lys
            595             600             605
Ile Thr Cys Met Asn Pro Ser Ala Tyr Gln Arg Thr Tyr Ser Met Lys
        610             615             620
Tyr Phe Lys Asn Ser Ser Ser Ala Lys Asp Asn Ser Ile Asn Thr Ser
625                 630             635                 640
Lys His Asp His Arg Trp Ser Arg Arg Trp Gln Glu Ser Arg Arg
            645             650             655
```